United States Patent
Müller et al.

(10) Patent No.: US 6,479,503 B2
(45) Date of Patent: Nov. 12, 2002

(54) CYCLOALKANO-INDOLE AND -AZAINDOLE DERIVATIVES

(75) Inventors: Ulrich Müller, Wuppertal (DE); Richard Connell, Trumbull, CT (US); Siegfried Goldmann, Wuppertal (DE); Rudi Grützmann, Solingen (DE); Martin Beuck, Nilford, CT (US); Hilmar Bischoff, Wuppertal (DE); Dirk Denzer, Wuppertal (DE); Anke Domdey-Bette, Hückeswagen (DE); Stefan Wohlfeil, Hilden (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/814,263

(22) Filed: Mar. 21, 2001

(65) Prior Publication Data

US 2002/0055635 A1 May 9, 2002

Related U.S. Application Data

(62) Division of application No. 09/313,035, filed on May 17, 1999, now Pat. No. 6,265,431, which is a division of application No. 08/887,781, filed on Jul. 3, 1997, which is a division of application No. 08/535,698, filed on Sep. 28, 1995, now Pat. No. 5,684,014.

(30) Foreign Application Priority Data

Oct. 4, 1994 (DE) .............................................. 4435477

(51) Int. Cl.$^7$ ..................... A61K 31/437; C07D 471/06

(52) U.S. Cl. ............................. 514/292; 546/85; 546/87
(58) Field of Search ....................... 546/85, 87; 514/292

(56) References Cited

U.S. PATENT DOCUMENTS

| 3,632,807 A | 1/1972 | Maurer et al. |
| 4,775,680 A | 10/1988 | Gillard et al. |
| 5,521,206 A | 5/1996 | Müller et al. |
| 5,684,014 A * | 11/1997 | Muller et al. ............... 514/292 |
| 5,776,964 A | 7/1998 | Müller et al. |
| 5,952,498 A | 9/1999 | Lenfers et al. |

FOREIGN PATENT DOCUMENTS

| EP | 0 234 708 A1 | 9/1987 |
| EP | 0 300 676 A2 | 1/1989 |
| EP | 0 310 179 A2 | 4/1989 |
| EP | 0 496 237 A2 | 7/1992 |
| EP | 0 509 359 | 10/1992 |
| EP | 0 617 035 A1 | 9/1994 |

OTHER PUBLICATIONS

Heterocycles, vol. 22, No. 10, 1984 (pp. 2277–2279).

* cited by examiner

*Primary Examiner*—Alan L. Rotman
*Assistant Examiner*—Rita Desai
(74) *Attorney, Agent, or Firm*—Norris McLaughlin & Marcus

(57) ABSTRACT

Cycloalcanoindole and -azaindole derivatives are prepared by reaction of appropriately substituted carboxylic acids with anmines. The cycloahloanindole and -azaindole derivatives are suitable as active compounds for medicaments, preferably antiatherosclerotic medicaments.

5 Claims, No Drawings

CYCLOALKANO-INDOLE AND -AZAINDOLE DERIVATIVES

CROSS-REFERENCE

This application is a Divisional of application Ser. No. 09/313,035 now U.S. Pat. No. 6,265,431 filed May 17, 1999, which is a division of application Ser. No. 08/887,781, filed Jul. 3, 1997, which is a division of application Ser. No. 08/535,698, filed Sep. 28, 1995, now U.S. Pat. No. 5,684,014.

The present invention relates to cycloalkano-indole and -azaindole derivatives, processes for their preparation and their use as medicaments, in particular as antiatherosclerotic medicarnents.

It is known that increased blood levels of triglycerides (hypertriglyceridaemia) and cholesterol (hypercholesterolaemia) are associated with the genesis of atherosclerotic vessel wall changes and coronary heart diseases.

A distinctly increased risk of the development of coronary heart disease is moreover present if these two risk factors occur in combination, which is accompanied, in turn, with an overproduction of apolipoprotein B-100. There is therefore, as before, a great need to make available effective medicarnents for the control of atherosclerosis and coronary heart diseases.

The present invention relates to cycloalkano-indole and -azaindole derivatives of the general formula (I)

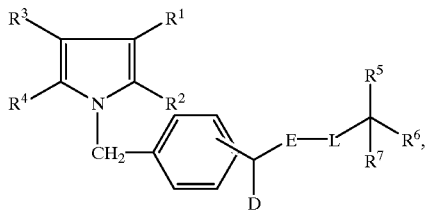

in which $R^1$ and $R^2$, including the double bond connecting them, together form a phenyl or pyridyl ring or a ring of the formula

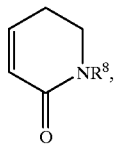

wherein $R^8$ denotes hydrogen or straight-chain or branched alkyl having up to 4 carbon atoms, $R^3$ and $R^4$, including the double bond connecting them, together form a phenyl ring or a 4- to 8-membered cycloaukene or oxocycloalkene radical, all ring systems mentioned under $R^1/R^2$ and $R^3/R^4$ optionally being substituted up to 3 times by identical or different halogen, trifluoromethyl, carboxyl or hydroxyl substituents, by straight-chain or branched alkoxy or alkoxycarbonyl each having up to 6 carbon atoms or by straiht-chain or branched alkyl having up to 6 carbon atoms, which, for its part, can be substituted by hydroxyl or by straight-chain or branched alkoxy having up to 4 carbon atoms, D represents hydrogen, cycloalkyl having 4 to 12 carbon atoms or straight-chain or branched alkyl having up to 12 carbon atoms, E represents the —CO— or —CS— group, L represents an oxygen or sulphur atom or a group of the formula —$NR^9$, wherein $R^9$ denotes hydrogen or straight-chain or branched alkyl having up to 6 catbon atoms, which is optionally substituted by hydroxyl or phenyl, $R^5$ represents phenyl or a 5- to 7-membered sated or unsaturated heterocycle having up to 3 heteroatoms from the series consisting of S, N and/or O, the cycles optionally being substituted up to 3 times by identical or different nitro, carboxyl, halogen or cyano substituents or by straight-chain or branched alkenyl or alkoxycarbonyl each having up to 6 carbon atoms or by staight-chain or branched alkyl having up to 6 carbon atoms, which is optionally substituted by hydroxyl, carboxyl or by straight-chain or branched alkoxy or alkoxycarbonyl each having up to 6 carbon atoms, and/or the cycles optionally being substituted by a group of the formula —$OR^{10}$ or —$NR^{11}R^{12}$, wherein $R^{10}$ denotes hydrogen or straight-chain or branched alkyl or alkenyl each having up to 6 carbon atoms, $R^{11}$ and $R^{12}$ are identical or different and denote phenyl, hydrogen or straight-chain or branched alkyl having up to 6 carbon atoms or straight-chain or branched acyl having up to 8 carbon atoms, which is optionally substituted by a group of the formula —$NR^{13}R^{14}$, wherein $R^{13}$ and $R^{14}$ are identical or different and denote hydrogen or straight-chain or branched acyl having up to 8 carbon atoms, $R^6$ represents hydrogen, carboxyl or straight-chain or branched alkoxycarbonyl having up to 5 carbon atoms, or represents straight-chain or branched alkyl having up to 6 carbon atoms, which is optionally substituted by hydroxyl or by a group of the formula —O—CO—$R^{15}$, wherein $R^{15}$ denotes phenyl which is optionally substituted up to 3 times by identical or different halogen or hydroxyl substituents or by straight-chain or branched alkyl having up to 5 carbon atoms, or straight-chain or branched alkyl or alkenyl each having up to 22 carbon atoms, each of which is optionally substituted by a group of the formula —$OR^6$, wherein $R^{16}$ is hydrogen, benzyl, triphenylmethyl or straight-chain or branched acyl having up to 6 carbon atoms, $R^7$ represents hydrogen or $R^6$ and $R^7$ together represent the group of the formula =O, if appropriate in an isomeric form and their salts.

The cycloalkan-indole and -azaindole derivatives according to the invention can also be present in the form of their salts. In general, salts with organic or inorganic bases or acids may be mentioned here.

In the context of the present invention, physiologically acceptable salts are preferred. Physiologically acceptable salts of the compounds according to the invention can be salts of the substances according to the invention with mineral acids, carboxylic acids or sulphonic acids. Particularly preferred salts are, for example, those with hydrochloric acid, hydrobrornic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts can also be metal or ammonium salts of the compounds according to the invention which have a free carboxyl group. Particularly preferred salts are, for example, sodium, potassium, magnesium or calcium salts, and also ammonium salts which are derived from ammonia, or organic amines, such as, for example ethylamine, di- or triethylamine, di- or triethanolamine, dicyclohexylamine, dimethylaminoethanol, arginine, lysine, ethylenediamine or 2-phenylethylamine.

Including the double bond of parent structure, the cycloalkene radical ($R^3/R^4$) in the context of the invention in general represents a 4-to 8-membered hydrocarbon radical, preferably a 5- to 8-membered hydrocarbon radical, for example a cyclobutene, cyclopentene, cyclohexene, cycloheptene or cyclooctene radical. The cyclopentene, cyclohexene, cyclooctene or cycloheptene radicals are preferred Heterocycle ($R^5$) in the context of the invention in general represents a saturated or unsaturated 5- to 7-membered heterocycle, preferably a 5- to 6-membered heterocycle, which can contain up to 3 heteroatoms from the series consisting of S, N and/or O. Examples which may be mentioned are: pyridyl, thienyl, furyl, pyrrolyl, thiazolyl, oxazolyl, imidazolyl, morpholinyl or piperidyl. Pyridyl and thienyl are preferred.

The compounds according to the invention can exist in stereoisomeric forms which either behave as image and mirror image (enantiomers), or do which do not behave as image and mirror image (diastereomers). The invention relates both to the enantiomers and diastereomers and their respective mixtures. These mixtures of the enantiomers and diastereomers can be separated in a known manner into the stereoisomerically uniform constituents.

Preferred compounds of the general formula (I) are those in which $R^1$ and $R^2$, including the double bond connecting them, together form a phenyl or pyridyl ring or a ring of the formula

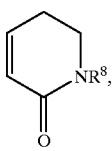

wherein $R^8$ denotes hydrogen or stright-chain or branched alkyl having up to 3 carbon atoms, $R^3$ and $R^4$, including the double bond connecting them, together form a phenyl ring or a cyclopentene, cyclohexene, cycloheptene, cyclooctene, oxocyclopentene, oxocyclohexene, oxocycloheptene or oxocyclooctene radical, all ring systems mentioned under $R^1/R^2$ and $R^3/R^4$ optionally being substituted up to 2 times by identical or different fluorine, chlorine, bromine, trifluoromethyl, carboxyl or hydroxyl substituents, by straight-chain or branched alkoxy or alkoxycarbonyl each having up to 4 carbon atoms or by straight-chain or branched alkyl having up to 4 carbon atoms, which, in turn, can be substituted by hydroxl or by straight-chain or branched alkoxy having up to 3 carbon atoms.

D represents hydrogen, cyclobutyl, cyclopentyl, cyclohexyl, cycloheptyl, cyclooctyl or straight-chain or branched alkyl having up to 10 carbon atoms, E represents the —CO— or —CS— group, L represents an oxygen or sulphur atom or represents a group of the formula —$NR^9$, wherein $R^9$ denotes hydrogen or staight-chain or branched alkyl having up to 5 carbon atoms, which is optionally substituted by hydroxyl or phenyl, $R^5$ represents phenyl, pyridyl, furyl, thienyl or imidazolyl, each of which is optionally substituted up to 2 times by identical or different nitro, carboxyl, fluorine, chlorine, bromine or cyano substituents, by straight-chain or branched alkenyl or alkoxy carbonyl each having up to 4 carbon atoms or by straight-chain or branched alkyl having up to 5 carbon atoms, which is optionally substituted by hydroxyl, carboxyl or by staight-chain or branched alkoxy or alkoxycarbonyl each having up to 5 carbon atoms, and/or the cycles are optionally substituted by a group of the formula —$OR^{10}$ or —$NR^{11}R^{12}$, wherein $R^{10}$ denotes hydrogen or straight-chain or branched alkyl or alkenyl each having up to 4 carbon atoms, $R^{11}$ and $R^{12}$ are identical or different and denote phenyl, hydrogen or straight-chain or branched alkyl having up to 5 carbon atoms or denote straight-chain or branched acyl having up to 6 carbon atoms, which is optionally substituted by a group of the formula —$NR^{13}R^{14}$, wherein $R^{13}$ and $R^{14}$ are identical or different and denote hydrogen or straight-chain or branched acyl having up to 6 carbon atoms, $R^6$ represents hydrogen carboxyl or straight-chain or branched alkoxycarbonyl having up to 4 carbon atoms, or represents straight-chain or branched alkyl having up to 5 carbon atoms, which is optionally substituted by hydroxyl or by a group of the formula —O—CO—$R^{15}$, wherein $R^{15}$ denotes phenyl which is optionally substituted up to 3 times by identical or different fluorine, chlorine, bromine or hydroxyl substituents or by straight-chain or branched alkyl having up to 4 carbon atoms, or straight-chain or branched alkyl or alkenyl each having up to 20 carbon atoms, each of which is optionally substituted by a group of the formula —$OR^{16}$, wherein $R^{16}$ is hydrogen, benzyl, triphenylmethyl or straight-chain or branched acyl having up to 5 carbon atoms, $R^7$ represents hydrogen or $R^6$ and $R^7$ together represent the group of the formula =O, if appropriate in an isomeric form, and their salts.

Particularly preferred compounds of the general formula (I) are those in which $R^1$ and $R^2$, including the double bond connecting them, together form a phenyl or pyridyl ring or a ring of the formula

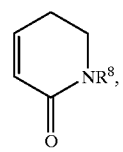

wherein

R⁸ denotes hydrogen or methyl,

R³ and R⁴, including the double bond connecting them, together form a phenyl ring or a cyclopentene, cyclohexene, cycloheptene, cyclooctene, oxocyclopentene, oxocyclohexene, oxocycloheptene or oxocyclooctene radical, all ring systems mentioned under R¹/R² and R³/R⁴ optionally being substituted up to 2 times by identical or different fluorine, chlorine, bromine, trifluoromethyl, carboxyl or hydroxyl substituents, by straight-chain or branched alkoxy or alkoxycarbonyl each having up to 3 carbon atoms or by straight-chain or branched alkyl having up to 3 carbon atoms, which, for its part, can be substituted by hydroxyl, methoxy or ethoxy, D represents hydrogen, cyclopentyl, cyclohexyl, cycloheptyl, cyclooctyl or straight-chain or branched alkyl having up to 6 carbon atoms, E represents the —CO— or —CS— group, L represents an oxygen or sulphur atom or represents a group of the formula —NR⁹, wherein R⁹ denotes hydrogen or straight-chain or branched alkyl having up to 4 carbon atoms, which is optionally substituted by hydroxyl or phenyl, R⁵ represents phenyl, pyridyl or thienyl, each of which is optionally substituted up to 2 times by identical or different nitro, carboxyl, fluorine, chlorine, bromine or cyano substituents, by straight-chain or branched alkenyl or alkoxycarbonyl each having up to 3 carbon atoms or by straight-chain or branched alkyl having up to 4 carbon atoms, which is optionally substituted by hydroxyl, carboxyl or by straight-chain or branched alkoxy or alkoxycarbonyl each having up to 4 carbon atoms, and/or the cycles are optionally substituted by a group of the formula —OR¹⁰ or —NR¹¹R¹², wherein R¹⁰ denotes hydrogen or straight-chain or branched alkyl or alkenyl each having up to 3 carbon atoms, R¹¹ and R¹² are identical or different and denote phenyl, hydrogen or straight-chain or branched alkyl having up to 4 carbon atoms or denote straight-chain or branched acyl having up to 5 carbon atoms, which is optionally substituted by a group of the formula —NR¹³R¹⁴, wherein R¹³ and R¹⁴ are identical or different and denote hydrogen or straight-chain or branched acyl having up to 5 carbon atoms, R⁶ represents hydrogen, carboxyl or straight-chain or branched alkoxycarbonyl having up to 3 carbon atoms, or represents straight-chain or branched alkyl having up to 4 carbon atoms, which is optionally substituted. by hydroxyl or by a group of the formula —O—CO—R¹⁵, wherein R¹⁵ denotes phenyl which is optionally substituted up to 3 times by identical or different straight-chain or branched alkyl having up to 3 carbon atoms, or denotes straight-chain or branched alkyl or alkenyl each having up to 19 carbon atoms, each of which is optionally substituted by a group of the formula —OR¹⁶, wherein R¹⁶ denotes hydrogen, benzyl, triphenylmethyl or straight-chain or branched acyl having up to 4 carbon atoms, R⁷ represents hydrogen or R⁶ and R⁷ together represent the group of the formula =O, if appropriate in an isomeric form, and their salts.

A process for the preparation of the compounds of the general formula (I) according to the invention has additionally been found, characterized in that carboylic acids of the general formula (II)

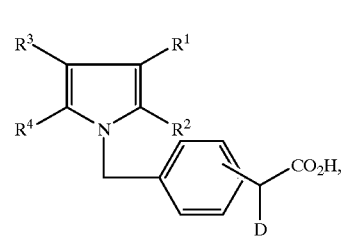

(II)

in which

R¹, R², R³, R⁴ and D have the meaning indicated, are amidated using compounds of the general formula (III)

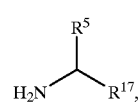

(III)

in which

R⁵ has the meaning indicated and

R¹⁷ has the indicated meanig of R⁶, but does not represent carboxyl, in an inert solvent and in the presence of bases and/or auxiliaries, and, if appropriate, functional groups are varied by hydrolysis, esterification or reduction.

The process according to the invention can be illustrated by the following reaction scheme:

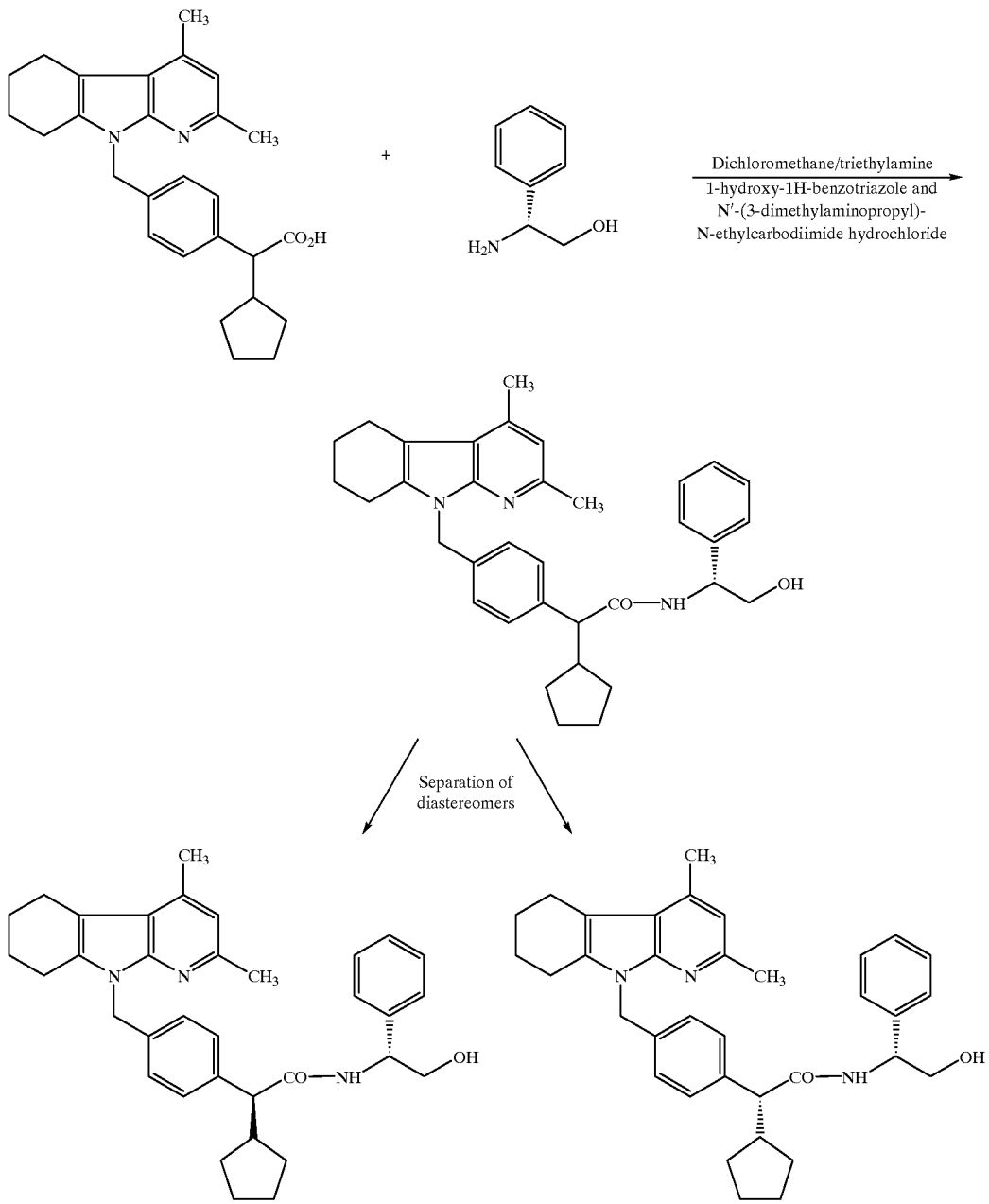

Suitable solvents for the amidation are in this case inert organic solvents which do not change under the reaction conditions. These include ethers, such as diethyl ether or tetrahydrofuran halogenohydrcarbons such as dichloromethane, trichloromethane, tetrachloromethane, trichloroethane, tetrachloroethane, 1,2-dichloroethane or trichloroethylene, hydrocarbons such as benzene, xylene, toluene, hexane, cyclohexane or petroleum fractions, nitromethane, dimethylformamide, acetone, acetonitrile or hexamethylphosphoramide. It is also possible to employ mixtures of the solvents. Dichloromethane, tetrahydrofuran, acetone and dimethylformamide are particularly preferred.

Bases which can be employed for the process according to the invention are in general inorganic or organic bases. These preferably include alkali metal hydroxides such as, for example, sodium hydroxide or potassium hydroxide, alkaline earth metal hydroxides, such as, for examnple, barium hydroxide, alkali metal carbonates such as sodium carbonate or potassium carbonate, alkaline earth metal carbonates such as calcium carbonate, or alkali metal alkoxides such as sodium or potassium methoxide, sodium or potassium ethoxide or potassium tert-butoxide, or organic amines (trialkyl($C_1$–$C_6$)amines) such as triethylamine, or heterocycles such as 1,4diazabicyclo[2.2.2]octane (DABCO), 1,8-diazabicyclo[5.4.0]undec-7-ene (DBU), pyridine, diaminopyridine, methylpiperidine or morpholine. It is also possible to employ alkali metals such as sodium and their hydrides such as sodium hydride as bases. Sodium and potassium carbonate and triethylamine are preferred.

The base is employed in an amount from 1 mol to 5 mol, preferably from 1 mol to 3 mol, relative to 1 mol of the compound of the general formula (II).

The reaction is in general carried out in a temperature range from 0° C. to 150° C., preferably from +20° C. to +110° C.

The reaction can be carried out at normal, increased or reduced pressure (e.g. 0.5 to 5 bar). In general, the reaction is carried out at normal pressure.

The amidation can optionally proceed via the activated stage of the acid halides, which can be prepared from the corresponding acids by reaction with thionyl chloride, phosphorus trichloride. phosphorus pentachloride, phosphorus tribromide or oxalyl chloride.

The abovementioned bases can optionally also be employed for the amidation as acid-binding auxiliaries.

Suitable auxiliaries are also dehydrating reagents. These include, for example, carbodiimides such as diisopropylcarbodiimide, dicyclohexylcarbodiimide and N-(3-dimethylaminopropyl)N'-ethylcarbodiimide hydrochloride or carbonyl compounds such as carbonyldiidazole or 1,2-oxazolium compounds such as 2-ethyl-5-phenyl-1,2-oxazolium-3-sulphonate or propanephosphonic anhydride or isobutyl chloroformate or benzotriazolyloxy-tris-dimethylamino)phosphonium hexafluorophosphate or diphenyl phosphoramidate or methanesulphonyl chloride, if appropriate in the presence of bases such as triethylamine or N-ethylmorpholine or N-methylpiperidine or dicyclohexylcarbodiimide and N-hydroxysuccinimide.

The acid-binding agents and dehydrating reagents are in general employed in an amount from 0.5 to 3 mol, preferably from 1 to 1.5 mol, relative to 1 mol of the corresponding carboxylic acids.

The variation of functional groups, for example hydrolysis, esterification and reduction, and also separation of isomers and salt formation is carried out by customary methods.

The carboxylic acids of the general formula (II) are new and can be prepared by reacting compounds of the general formula (IV)

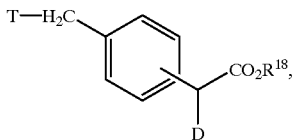

(IV)

in which
D has the meaning indicated,
T represents a typical leaving group, for example chlorine, bromine, iodine, tosylate or mesylate, preferably bromine,
and
$R^{18}$ represents $(C_1-C_4)$-alkyl, with compounds of the general formula (V)

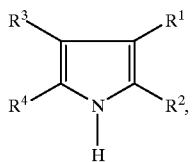

(V)

in which
$R^1$, $R^2$, $R^3$ and $R^4$ have the meaning indicated, in inert solvents, if appropriate in the presence of a base.

Suitable solvents for the process are the customary organic solvents which do change under the reaction conditions. These preferably include ethers such as diethyl ether, dioxane, tetrahydrofuran, glycol dimethyl ether, or hydrocarbons such as benzene, toluene, xylene, hexane, cyclohexane or petroleum fractions, or halogenohydrocarbons such as dichloromethane, trichloromethane, tetrachloromethane, dichloroethylene, trichloroethylene or chlorobenzene, or ethyl acetate, triethylamine, pyridine, dimethyl sulphoxide, dimethylformamide, hexamethylphosphoramide, acetonitrile, acetone or nitromethane. It is also possible to use mixtures of the solvents mentioned. Dimethylformamide and tetrahydrofuran are preferred.

The bases employed for the process according to the invention can in general be inorganic or organic bases. These preferably include alkali metal hydroxides, for example, sodium hydroxide or potassium hydroxide, alkaline earth metal hydroxides, for example, barium hydroxide, alkali metal carbonates such as sodium carbonate or potassium carbonate, alkaline earth metal carbonates such as calcium carbonate, or alkali metal alkoxides such as sodium or potassium methoxide, sodium or potassium ethoxide or potassium tert-butoxide, or organic amines (trialkyl$(C_1-C_6)$ amines) such as triethylamine, or heterocycles such as 1,4diazabicyclo[2.2.2]octane (DABCO), 1,8-diazabicyclo[5.4.0]undec-7-ene (DBU), pyridine, diamninopyridine, methylpiperidine or morpholine. It is also possible to employ alkali metals such as sodium or their hydrides such as sodium hydride as bases. Sodium hydride, potassium carbonate, triethylamine, pyridine and potassium tert-butoxide, DBU or DABCO are preferred.

In general, the base is employed in an amount from 0.05 mol to 10 mol, preferably from 1 mol to 2 mol, relative to 1 mol of the compound of the formula (IV).

The process according to the invention is in general carried out in a temperature range from −30° C. to +100° C., preferably from −10° C. to +60° C.

The process according to the invention is in general carried out at normal pressure. However, it is also possible to carry out the process at elevated pressure or at reduced pressure (e.g. in a range from 0.5 to 5 bar).

The compounds of the general formula (III) are known per se.

The compounds of the general formula (IV) are known or can be prepared in analogy to known methods.

The compounds of the general formula (V) are known or can be prepared in analogy to known methods.

The compounds of the general formula (I) according to the invention have an unforeseeable spectrum of pharmacological action.

They can be used as active compounds in medicaments for the reduction of changes to vessel walls and for the treatment of coronary heart disorders, cardiac insufficiency, brain power disorders, ischaernic brain disorders, apoplexy, circulatory disorders, disorders of the microcirculation and thromboses.

Furthermore, the proliferation of smooth muscle cells plays a decisive part in the occlusion of vessels. The compounds according to the invention are suitable for inhibiting this proliferation and thus preventing atherosclerotic processes.

The compounds according to the invention are distinguished by a lowering of the ApoB-100-associated lipoproteins (VLDL and its degradation products, e.g. LDL), of ApoB-100, of triglycerides and of cholesterol. They thus have useful, superior pharmacological properties in comparison with the prior art.

Surprisingly, the action of the compounds according to the invention consists first in a decrease or complete inhibition of the formation and/or the release of ApoB-100-associated lipoproteins from liver cells, which results in a lowering of the VLDL plasma level. This lowering of VLDL must be accompanied by a lowering of the plasma level of ApoB100, LDL, triglycerides and cholesterol; a number of the above-mentioned risk factors which are involved in vessel wall changes are thus simultaneously decreased.

The compounds according to the invention can therefore be employed for the prevention and treatment of atherosclerosis, obesity, pancreatitis and constipation.

I Inhibition of the release of ApoB-100 Associated Lipopnteins

The test for detecting the inhibition of the release of ApoB-100-associated lipoproteins from liver cells was carried out in vitro using cultured liver cells, preferably using cells of the human line HepG2. These cells are cultured under standard conditions in medium for the culture of eukaryotic cells, preferably in RPMI 1640 With 10% foetal calf serum. HepG2 cells synthesize and secrete into the culture supernatant ApoB-100-associated lipoprotein particles which in principle are built up in a similar manner to the VLDL and LDL particles which are to be found in the plasma These particles can be detected using an immunoassay for human LDL. This immunoassay is carried out using antibodies which have been induced against human LDL in rabbits under standard conditions. The anti-LDL antibodies (rabbit anti-LDL Ab) wevere purified by affiity chromatography on an inunuosorbent using human LDL. These purified rabbit anti-LDL Ab are adsorbed on the surface of plastic. Expediently, this adsorption is carried out on the plastic surface of microtitre plates having 96 wells, preferably on MaxiSorp plates. If ApoB-100-associated particles are present in the supernatant of HeG2 cells, they can be bound to the insolubilized rabbit anti-LDL Ab, and an immune complex results which is bound to the plastic surface. Unbound proteins are removed by washing. The immune complex located on the plastic surface is detected using monoclonal antibodies which have been induced against human LDL and purified according to standard conditions. These antibodies were conjugated with the enzyme peroxidase. Peroxidase converts the colourless substrate TMB into a coloured product in the presence of $H_2O_2$. After acidification of the reaction mixture with $H_2SO_4$, the specific light absorption at 450 nm is deteminèd, which is a measure of the amount of ApoB-100associated particles which have been secreted into the culture supernatant by the HepG2 cells.

Surprisingly, the compounds according to the invention inhibit the release of the ApoR100-associated particles. The $IC_{50}$ value indicates at which substance concentration the light absorption is inhibited by 50% in comparison with the control (solvent control without substance).

| Ex. No. | $IC_{50}$ [$10^{-9}$ mol/l] |
| --- | --- |
| 1 | 28 |
| 5 | 1.1 |
| 31 | 170 |
| 50 | 29 |

2. Determination of the VLDL Secretion in vivo in the Hamster

The effect of the test substances on VLDL secretion in vivo is investigated in the hamster. To do this, golden hamsters are anaesthetized with Ketaset (83 mg/kg s.c.) and Nembutal (50 mg/kg i.p.) after premedication with atropine (83 mg/kg s.c.). When the animals have become reflex-free, the jugular vein is exposed and cannulated. 0.25 ml/kg of a 20% strength solution of Triton WR-1339 in physiological saline solution is then administered. This detergent inhibits the lipoprotein lipase and thus leads to a rise in the triglyceride level as a result of a lack of catabolism of secreted VLDL particles. This triglyceride rise can be used as a measure of the VLDL secretion rate.

Blood is taken from the animals before and also one and two hours after administration of the detergent by puncture of the retroorbital venous plexus. The blood is incubated for two hours at room temperature, and then overnight at 4° C., in order to end clotting completely. It is then centrifuged at 10,000 g for 5 minutes. The triglyceride concentration in the serum thus obtained is determined with the aid of a modified commercially available enzyme test (Merckotest® triglyceride No. 14354). 100 $\mu$l of serum are treated with 100 $\mu$l of test reagent in 9whole plates and incubated at room temperature for 10 minutes. The optical density is then determined at a wavelength of 492 nM in an automatic plate-reading apparatus (SLT Spectra). Serum samples having an excessively high triglyceride concentration are diluted with physiological saline solution. The triglyceride concentration contained in the samples is determined with the aid of a standard curve measured in parallel. In this model, test substances are administered intravenously either immediately before administration of the detergent or orally or subcutaneously before initiation of anaesthesia.

| Ex. No. | $ED_{50}$ [mg/kg] p.o. |
| --- | --- |
| 2 | 10–15 |
| 5 | 3–6 |
| 7 | 10–20 |

3. Inhibition of Intestinal Triglyceride Absorption in vivo (Rats)

The substances which are to be investigated for their triglyceride absorption-inhibiting action in vivo are administered orally to male Wistar rats having a body weight of between 170 and 230 g. For this purpose, the animals are divided into groups of 6 animals 18 hours before substance administration and food is then withdrawn from them. Drking water is available to the animals ad libitum The animals of the control groups receive an aqueous tragacanth suspension or a tragacanth suspension which contains olive oil. The tragacanth-olive oil suspension is prepared using an Ultra-Turrax. The substances to be investigated are suspended in an appropriate tragacanth-olive oil suspension likewise using the Ultra-Turrax, directly before substance administration.

To determine the basal serum triglyceride content, blood is taken from each rat by puncture of the retroorbital venous plexus before stomach tube application. The tragacanth suspension, the tragacanth-olive oil suspensions without substance (control arimals) or the substances suspended in an appropriate tragacanth-olive oil suspension are then administered to the fasting animals using a stomach tube. Further taking of blood to determine the postprandial serum triglyceride rise is carried out, as a rule, 1, 2 and 3 hours after stomach tube application.

The blood samples are centrifuged and, after recovering the serum, the triglycerides are determined photometrically using an EPOS analyzer 5060 (Eppendorf Geratebau, Netheler & Hinz GmbH, Hamburg). The determination of the triglycerides is carried out completely enzymatically using a standard commercial UV test.

The postprandial serum triglyceride rise is determined by subtraction of the triglyceride preliminary value of each animals from its corresponding postprandial triglyceride concentrations (1, 2 and 3 hours after administration).

The differences (in mmouL/) at each point in time (1, 2 and 3 hours) are averaged in the groups, and the mean values of the serum triglyceride rise (Δ TG) of the substance-treated animals is compared with the animals which only received the tragacanth-oil suspension.

The serum triglyceride course of the control animals which only received tragacanth is also calculated. The substance effect at each point in time (1, 2 and 3 hours) is determined as follows and indicated in Δ% of the oil-loaded control.

$$\Delta\% \text{ Triglyceride rise} = \frac{\Delta TG_{substance} - \Delta TG_{tragacanth\ control}}{\Delta TG_{oil\ loading} - \Delta TG_{tragacanth\ control}} \times 100$$

Effect of 10 mg of test substance/kg of body weight p.o. on the triglyceride rise (Δ%) 2 h after a triglyceride loading in the serum of fasting rats. Tlhe serum triglyceride rise of fat-loaded control animals relative to the serum triglyceride level of tragacanth control animals corresponds to 100%. n=6 animals per group.

| | Serum triglyceride rise in % (2 h pp) |
|---|---|
| Triglyceride loading | 100 |
| Tragacanth control | 0 |
| Substance 10 mg/kg of body weight p.o. | |
| Ex. No. 10 | 34 |
| Ex. No. 66 | 67 |
| Ex. No. 54 | 54 |
| Ex. No. 71 | 18 |
| Ex. No. 5 | −16 |
| Ex. No. 20 | 35 |

Statistical evaluation is carried out using Student's t test after preliminary checking of the variances for homogeneity.

Substances which at one point in time statistically significantly ($p<0.05$) decrease the postprandial serun triglyceride rise by at least 30% compared with the untreated control group are regarded as pharmacologically active.

4. Inhibition of VLDL Secretion in vivo (Rats)

The action of the test substances on VLDL secretion is likewise investigated in the rat. To do this, 500 mg/kg of body weight (2.5 mgkg) of Triton WR-1339, dissolved in physiological saline solution, is administered intravenously into the tail vein of rats. Triton WR-1339 inhibits lipoprotein lipase and thus leads to an increase in the triglyceride and cholesterol level by inhibition of the VLDL catabolism. These rises can be used as a measure of the VLDL secretion rate.

Blood is taken from the animals by puncture of the retroorbital venous plexus before and also one and twvo hours after administration of the detergent. The blood is incubated at room temperature for 1 h for clotting and the serum is obtained by centrifugation at 10,000 g for 20 s. The triglycerides are then photometrically determined by means of a standard commercial coupled enzyme test (Sigma Diagnostics®, No. 339) at a wavelength of 540 nm Measurement is carried out with the aid of a likewise coupled enzyme test (Boehring Mannheim®, No. 1442350) at a wavelength of 546 nm. Samples with triglyceride or cholesterol concentrations which exceed the measuring range of the methods are diluted with physiological saline solution. The determination of the respective serum concentrations is carried out with the aid of standard series measured in parallel. Test substances are administered orally, intravenously or subcutaneously immediately after the Triton injection.

The invention additionally relates to the combination of cycloalkano-indole and -azaindole derivatives of the general formula (1) with glucosidase and/or amylase ihibitor for the treatment of familial hyperlipidaemia, obesity (adiposity) and diabetes mellitus. Glucosidase and/or amylase inhibitors in the context of the invention are, for example, acarbose, adiposine, voglibase, miglitol, emiglitate, MDL 25637, camialibase (MDL 73945), tendamistat, AI-3688, trestatin, pradimnilin-Q and salbostatin.

Combination of acarbose, miglitol, emiglitate or voglibase with one of the abovementioned compounds of the general formula (I) according to the invention is preferred.

The new active compounds can be converted in a known manner into the customary formulations, such as tablets, coated tablets, pills, granules, aerosols, syrups, emulsions, suspensions and solutions, using inert, non-toxic, pharmaceutically suitable excipients or solvents. In this case, the therapeutically active compound should in each case be present in a concentration of approximately 0.5 to 90% by weight of the total mixture, i.e. in amounts which are sufficient in order to achieve the dosage range indicated.

The formulations are prepared, for example, by extending the active compounds with solvents and/or excipients, if appropriate using emulsifiers and/or dispersants, it optionally being possible, e.g. in the case of the use of water as a diluent, to use organic solvents as auxiliary solvents.

Administration is carried out in a customary manner, preferably orally or parenterally, in particular perlingually or intravenously.

In the case of parenteral administration, solutions of the active compound can be employed using suitable liquid vehicles.

In general, it has proved advantageous in the case of intravenous adminstration to administer amounts of approximately 0.001 to 1 mg/k of body weight, preferably approxijmaely 0.01 to 0.5 mg/kg of body weight, to achieve effective results, and in the case of oral adrministration the dose is approximately 0.01 to 20 mg/kg of body weight, preferably 0.1 to 10 mg/kg of body weight.

In spite of this, it may optionally be necessary to depart from the amounts mentioned, namely depending on the body weight or on the type of administration route, on individual behaviour towards the medicament, the manner of its formulation and the time or interval at which administration takes place. Thus, in some cases it may be adequate to manage with less than the abovementioned minimum amount. while in other cases the upper limit mentioned must be exceeded. In the case of the administration of larger amounts, it may be advisable to divide these into several individual doses over the course of the day.

Definition of the Isomer Types:
4 dia=mixture of the four possible diastereomers in the case of two centres of asymmetry in the molecule
dia A=diastereomer having the larger $R_f$ value
dia B=diastereomer having the smaller $R_f$ value
ent=enantiomer 2 ent dia=mixture of two enantiomerically pure diastereomers
ent dia A=enantiomerically pure diastereomer having the larger $R_f$ value
ent dia B=enantiomerically pure diastereomer having the smaller $R_f$ value
R=R enantiomer
rac=racernate
rac dia A=racemic diastereomer having the larger $R_f$ value
rac dia B=racermic diastereomer having the smaller $R_f$ value
S=S enantiomer
Abbevations Used:
Ac=acetyl
Bn=benzyl
Bz=benzoyl
iB=isobutyl
nBu=normnal butyl
sBu=secondary butyl
tBu=tertiary butyl
DDQ=2,3-dichloro-5,6dicyano-1,4benzoquinone
cDec=cyclodecyl
DMF=N,N-dimethylformamide
DMSO=dimethyl sulphoxide
cDodec=cyclododecyl
Et=ethyl
cHept=cyclo-heptyl
cHex=cyclo-hexyl
HOBT=1-hydroxy-1H-benzotriazole
Me=metlyl
Mes=mesyl
cNon=cyclo-nonyl
cOct=cyclo-octyl
cPent=cyclo-pentyl
nPent=normal pentyl
Ph=phenyl
cPr=cyclo-propyl
nPr=normal propyl
iPr=isopropyl
THF=tetrahydrofuran
TMS=tetramethylsilane
pTol=para-tolyl
pTos=para-tosyl
cUndec=cyclo-undecyl
Solvent Symbol
Dichloromethane: methanol=20:1 A
Dichloromehane: methanol=50:1 B
Dichloromethane: ethanol=20:1 C
Dichiorometiane: ethanol=50:1 D
Petroleum ether: ethyl acetate=1:1 E
Dichloromethane: methanol: acetic acid=90:10:2 F
Petroleum ether: ethyl acetate=2:1 G
Petroleum ether: ethyl acetate=10: 1 H
Toluene I
Toluene: ethyl acetate=1:1 K
Petroleum ether: ethyl acetate=5:1 L
Dichloromethane M
Petroleum ether: ethyl acetate=20:1 N
Dichloromethane: methanol 10:1 0
Cyclohexane: ethyl acetate=1: 1 p
Toluene: ethyl acetate=9:1 Q
Toluene: ethyl acetate=8:1 R
Petroleum ether: ethyl acetate=1:2 S
Dichloromethane: ethanol=5:1 T
Dichloromethane: ethanol=10:1 U
Preparion Procedure for the TLC Mobile Phase BABA:
87.9 ml of an aqueous 0.06667 molar potassium dihydrogen phosphate solution and 12.1 ml of an aqueous 0.06667 molar disodium hydrogen phosphate solution are mixed 60 ml of the solution prepared in this way are shaken with 200 ml of n-butyl acetate, 36 ml of n-butarol and 100 ml of glacial acetic acid and the aqueous phase is removed. The organic phase is the mobile phase BABA.

Starting Compomds

EXAMPLE I

1-Allyloxy-2-chloromethylbenzene

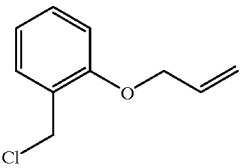

11.5 g (70 mmol) of 1-allyloxy-2-hydroxymethyl-benzene are treated with 11.6 ml (84 mmol) of triethylamine at 0° C. in 110 ml of dichloromethane and then slowly reacted with 5.4 ml (70 mmol) of methanesulphonyl chloride. After 4 hours, the mixture is extracted several times with water, and the organic phase is dried over magnesium sulphate and evaporated. Residual solvent is removed in a high vacuum
Yield: 8.5 g
$R_f$=0.23 (dichloromethane: ethanol 20: 1)

EXAMPLE II (2-Allyloxy-benzyl)amine

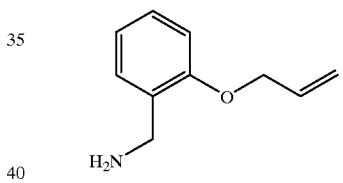

3 0 g (16.4 mmol) of the compound from Example I are boiled under reflux for 17 hours in 250 ml of a saturated methanolic ammonia solution. The reaction mixture is evaporated in vacuo, the residue is taken up in methanol and the mixture is evaporated again; this process is repeated a few times. The crude product is taken up in dichioromethane and extracted several times with water. The aqueous phase is evaporated to a vey great extent, an oil being obtained which crystallizes on standing.
Yield: 0.454 g (crude)
The product is reacted further without further purification.
$R_f$=0.41 (mobile phase: BABA)

EXAMPLE III

6-Chloro-2,4lutidine

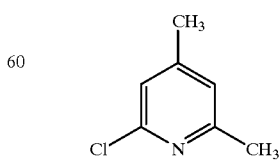

For the preparation of the title compound [US 36 32 807], 600 g (4.91 mol) of 6-amino-2,4lutidine are dissolved in 2

1 of methanol and the solution is saturated with hydrogen chloride gas at about 0° C. 1.3071 (9.82 mol) of isopentyl nitrite are added dropwise (about 2.5 h) at an internal temperate of below 10° C. and the mixture is left in this way for 15 h ,while warming to room temperature (about 25° C.). The solution is largely freed from the solvent in vacuo, mixed with 3 l of dichloromethane and 1.5 l of water and adjusted to pH=9.5 awhle cooling (<20° C.) with concentrated aqueous ammonia solution. The separated organic phase is dried with sodium sulphate, first concentrated in vacuo on a rotary evaporator and then distilled through a Vigreux column:

Fraction 1) B.p.=47–49° C. (12 mm Hg), 603 g
Fraction 2) B.p.=82–85° C. (12 mm Hg), 612 g (about 88% crude)
$R_f$=0.39 (petroleum ether: ethyl acetate=10:1)
$^1$H-NMR (CDCl$_3$ 200 MHz, TMS): δ=2.28 (S, 3 H), 2.47 (S, 3 H), 6.88 (S, 1 H), 6.96 (S, 1 H) ppm.

The crude product, which may contain small amounts of 6methoxy-2,4lutidine, is reacted further without further purification. Example IV 6-Hydrazino-2,4-lutidine (4,6-dimethyl-2-hydrazino-pyridine)

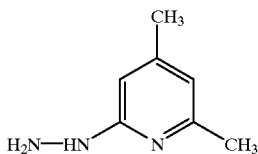

580 g (4.10 mol) of the compound from Example III are dissolved in 800 ml of diethylene glycol and the solution is stirred with 1050 ml of hydrazine hydrate for 48 h at a bath temperature of about 140° C. The cooled mixture is poured into 4.5 l of ether and 4.5 l of water and the organic phase is extracted twice with 2.3 l of dichloromethane each time. The combined organic phases are dried with sodium sulphate and evaporated in vacuo. 784 g of solvent containing crude product are obtained, which is reacted further without working up.
$R_f$=0.37 (dichloromethane: methanol=10:1)
$^1$H-NMR (d$_6$—DMSO, 250 MHz, TMS): δ=2.13 (S, 3 H), 2.22 (S, 3 H), 4.02 (S, 2 H), 6.26 (S, 1 H), 6.35 (S, 1 H), 7.11 (S, 1 H) ppm.

Example V

2-Hydrazino4-picoline (2-hydrazino-4-methylpyridine)

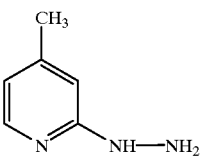

In analogy to the procedure of Example IV, 2-hydrazino-4-picoline is prepared from 2-chloro4-picoline.
$R_f$=0.06 (dichloromethane: methanol=10:1)

Example VI 2,4Dimethyl-5,6,7,8-tetrahydro-α-carboline

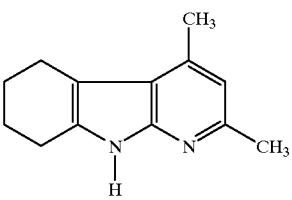

78 g (at most 0.49 mol) of crude compound from Example IV are reacted with 59 ml (0.56 mol) of cyclohexanone at room temperature (about 25° C.), whereon the internal temperature rises. After 2 h, the starting material has disappeared (TLC checking, dichloromethane: methanol=10:1). The mixture is taken up in 40 ml of diethylene glycol and reacted under reflux, constituents having a boiling point lower than the solvent (e.g. water of reaction and excess cyclohexanone) being removed by distillation (water separator). After 3 h, the intermediate hydrazone has disappeared (TLC checking, petroleum ether: ethyl acetate=1:1); the reaction mixture is cooled to room temperature and stirred with acetone. The precipitate obtained is filtered off with suction, washed with acetone and dried in vacuo (34.4 g). The largely solvent-free mother liquors are again treated with acetone, a further 9.3 g of product being obtained (total yield over three stages: 43.7 g/0.22 mol/ 47%).
M.p.: 248° C. (uncorrected)
$R_f$=0.41 (dichloromethane: methanol=20:1)
$^1$H-NMR (d$_6$-DMSO, 200 MHz, TMS): δ=1.78 (M, 4 H), 2.40 (S, 3 H), 2.48 (S, 3 H ), 2.64 (M, 2 H), 2.82 (M, 2 H), 6.57 (S, 1 H), 10.84 (S, 1 H) ppm.

The compounds of Table I are prepared analogously to the procedure of Example VI.

TABLE I

| Ex. No. | | $R_f$ (solvent) | Starting material (hydrazine*) |
|---|---|---|---|
| VII | (structure) | 0.59 (A) | Ex. No. IV |

TABLE I-continued

| Ex. No. | Structure | $R_f$ (solvent) | Starting material (hydrazine*) |
|---|---|---|---|
| VIII | 4-CH₃, 2-CH₃ cycloheptyl-fused pyrrolo-pyridine | 0.36 (E) | Ex. No. IV |
| IX | 4-CF₃, 2-CH₃ cyclohexyl-fused pyrrolo-pyridine | 0.45 (G) | |
| X | 2-CH₃ cyclohexyl-fused pyrrolo-pyridine | 0.46 (E) | |
| XI | 4-CH₃, 2-CH₃ cyclohexyl-fused indole | 0.06 (L) | |
| XII | 4-CH₃, 2-CH₃ cyclohexyl-fused pyrrolo-pyridine | 0.41 (E) | |
| XIII | 4-CH₃, 2-CH₃ cycloheptyl-fused pyrrolo-pyridine | 0.40 (E) | |
| XIV | cyclopentyl-fused pyrrolo-pyridine | 0.59 (O) | |
| XV | cycloheptyl-fused pyrrolo-pyridine | 0.34 (E) | |

TABLE I-continued

| Ex. No. | | $R_f$ (solvent) | Starting material (hydrazine*) |
|---|---|---|---|
| XVI | (structure) | 0.42 (E) | |
| XVII | (structure) | 0.59 (G) | |
| XVIII | (structure) | 0.85 (G) | |

Example XIX 2,4Dimethyl-α-carboline

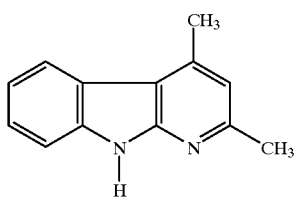

100 g (499 mmol) of the compound from Example VI are reacted under reflux with 164 ml (1 mol) of diethyl fumarate on 52 g of palladium (5% on carbon) in 700 ml of diethylene glycol. A small amount of ethanol distils off at the high internal temperature (if desired use a water separator). After about 8 h ,the starting material has disappeared (TLC checking, petroleum ether: ethyl acetate 1:1, detection in an iodine chamber). The cooled mixure is treated with 3 l of acetone, boiled, filtered off hot with suction through a clarifying filter (Seitz) and washed with 1 l of hot acetone. On cooling a precipitate is obtained which yields 58.3 g of product after filtering with suction, rinsing with cold acetone and drying in vacuo. The mother liquor is largely freed from acetone in vacuo, the precipitate which is deposited being worked up as above (9.4 g). The filtrate is again freed from acetone; after addition of n-pentane, product precipitates a further time (3.1 g/working up see above); total yield 72%.
M. p. 220–221° C. (uncorrected)
$R_f$=0.47 (petroleum ether: ethyl acetate=1:1)

$^1$H-NMR ($d_6$-DMSO, 200 MHz, TMS): δ=2.54 (S, 3 H), 2.75 (S, 3 H), 6.89 (S, 1 H), 7.20 (M, 1 H), 7.40 (M, 1 H), 7.48 (DD, 1 H), 8.05 (DD, 1 H), 11.61 (S, 1 H) ppm.

EXAMPLE XX tert-Butyl 4methylphenyl-acetate

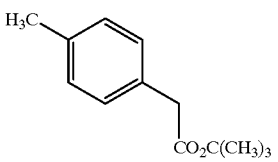

450 g (3 mol) of 4-methylphenyl-acetic acid (Aldrich), 1.13 l (12 mol) of tert-butanol and 90 g (0.74 mol) of 4-,(N,N- dimethylamino)pyridine are dissolved in 2 l of dichloromethane. After addition of 680 g (3.3 mol of dicyclohexylcarbodiimide, dissolved in 400 ml of dichloromethane, the mixture is stirred at 25° C. for 20 h, the precipitated urea is filtered off with suction and washed with 200 ml of dichloromethane, and the organic phase is washed twice each with 500 ml of 2 M hydrochloric acid and water. The organic phase is concentrated and distilled.

Yield: 408 g (66% of theory)
Boiling point: 73–78° C./0.2 mm

Example XXI tert-Butyl 2-Cyclopentyl-2-(4methlphenyl)acetate

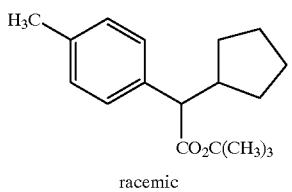

racemic 33.5 g (0.3 mol of potassium tert-butoxide are initially introduced into 100 ml of anhydrous DMF at 0° C., and 51.6 g (0.25 mol) of the compound from Example XX in 250 ml of anhydrous DMF are added dropwise. The mixture is stirred at 0° C. for 30 min and 32.2 ml (0.3 mol) of cyclopentyl bromide in 150 ml of anhydrous DMF are added dropwise at 5–15° C. and the mixture is stirred at 25° C. for 20 h. After concentrating, the residue is partitioned between water and diethyl ether, and the ether phase is dried over sodium sulphate and concentrated. The product crystallizes out.
Yield: 67 g (97.5% of theory)
Solidification point: 51–53° C.

The compounds of Table II are prepared in analogy to the procedure of Example XXI:

TABLE II

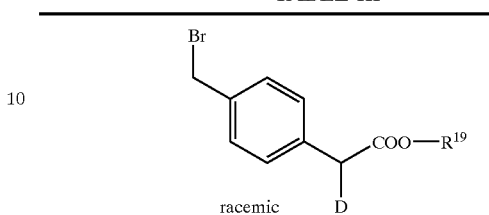

racemic

| Ex. No. | D | $R^{19}$ | $R_f$ (solvent) | Starting material* |
|---|---|---|---|---|
| XXII | cHex | tBu | 0.71 (I) | Ex. No. XX |
| XXIII | cHept | tBu | 0.32 (I) | Ex. No. XX |
| XXIV | iPr | $CH_3$ | 0.86 (Q) | sigma |
| XXV | iBu | tBu | 0.84 (R) | Ex. No. XX |
| XXVI | cPent | $CH_3$ | 0.59 (H) | sigma |
| XXVII | cHept | $CH_3$ | 0.57 (I) | sigma |

Example XXVIII tert-Butyl 2-(4-bromomethyl-phenyl)2-cyclopentyl-acetate

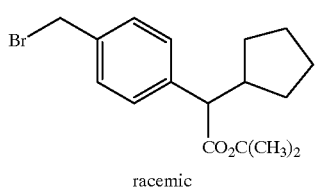

racemic 27.4 g (0.1 mol) of the compound from Example XXI are dissolved in 200 ml of tetrachloromethane and the solution is heated to boiling. After addition of 0.82 g of azobisisobutyronitrile, 18.7 g (0.105 mol) of N-bromosuccilimide are added in portions and the mixture is then refluxed for 1 h, cooled to 0° C. and succinimide is filtered off. After concentrating the filtrate the product precipitates. It is washed with petroleum ether (40/60) and dried.

Yield: 20 g (57% of theory)
M.p.: 73–76° C.

The compounds of Table III are prepared analogously to the procedure of Example XXVIII:

TABLE III

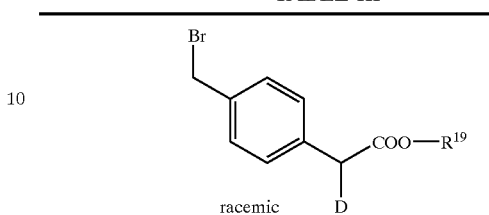

racemic

| Ex. No. | D | $R^{19}$ | $R_f$ (solvent) | Starting material* (Syn. from Ex. No.) |
|---|---|---|---|---|
| XXIX | cHex | tBu | 0.58 (H) | Ex. No. XXII |
| XXX | cHept | tBu | 0.84 (M) | Ex. No. XXIII |
| XXXI | iPr | $CH_3$ | 0.78 (M) | Ex. No. XXIV |
| XXXII | iBu | tBu | 0.86 (M) | Ex. No. XXV |
| XXXIII | cPent | $CH_3$ | 0.63 (H) | Ex. No. XXVI |
| XXXIV | cHept | $CH_3$ | 0.59 (I) | Ex. No. XXVII |

EXAMPLE XXXV tert-Butyl 2(R,S)2-cyclopentyl-2-[4 (2,4dimethyl-α-carbolin-9-yl)methyl]phenyl-acetate

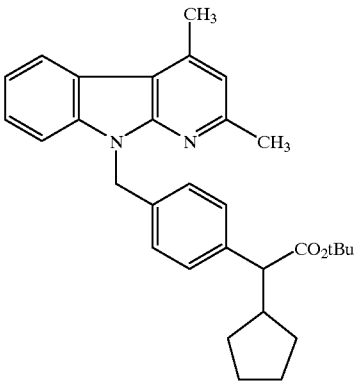

73.6 g(375 mmol) of the compound from Example XIX are reacted at 25° C. for 30 min with 42.13 g (375 mmol) of potassium tert-butoxide in 700 ml of anhydrous N,N-dimethylformamide and the mixture is then treated with 161.7 g (375 mmol) of the compound from Example XXVIII, dissolved in 680 ml of anhydrous N,N-dimethylformamide. The reaction is complete after 1 h (TLC checking, petroleum ether : ethyl acetate=10: 1). For working up, 2 l of buffer solution (pH =4/Merck) and 2 l of water are added, the precipitate which is deposited is filtered off, washed with water and again filtered off rapidly. The moderately damp solid is then stirred succesively with petroleum ether and methanol and filtered off with suction. Vacuum drying over phosphorus pentoxide yields 139.8 g (298 mmol/79%) of product.
M.p.:160–161° C. (uncorrected).
is $R_f$=0.39 (petroleum ether : ethyl acetate=10:1)
$^1$H-NMR (CDCl$_3$, 250 Mhz TMVS): δ=0.91 (M 1 H), 1.18–1.68 M 6 H), 1.87 M 1 H), 1.47 (S, 9 H), 2.42 (M 1 H),2.66 (S, 3 H), 2.83 (S, 3 H) 3.09 (D, 1 H), 5.67 (S, 2 H), 6.88 (S, 1 H), 7.13–7.41 (M 7 H), 8.09 (D, 1 H), 1H) ppm.

The compounds of Tables IV and V are prepared analogously to the procedure of Example XXXV:

TABLE IV

[Structure: racemic compound with Z-CH2-phenyl-CH(D)(CO2tBu)]

| Ex. No. | Z | D | $R_f$ (solvent) | Starting material (Syn. from Ex. No.) |
|---|---|---|---|---|
| XXXVI | [4-CH3, 2-CH3, N-CH3 tetrahydro-pyrido-indole] | cPent | 0.28 (H) | Benzyl bromide: Ex. No. XXVII<br>Heterocycle: Ex. No. VI |
| XXXVII | [4-CH3, 2-CH3, N-CH3 pyrido-indole] | cHept | 0.47 (H) | Benzyl bromide: Ex. No. XXX<br>Heterocycle: Ex. No. XIX |
| XXVIII | [4-CH3, 2-CH3, N-CH3 cyclopenta-pyrido-indole] | cHept | 0.54 (L) | Benzyl bromide: Ex. No. XXX<br>Heterocycle: Ex. No. VII |
| XXXIX | [4-CH3, 2-CH3, N-CH3 tetrahydro-pyrido-indole] | cHept | 0.27 (H) | Benzyl bromide: Ex. No. XXX<br>Heterocycle: Ex. No. VI |
| XL | [4-CH3, 2-CH3, N-CH3 cyclohepta-pyrido-indole] | cPent | 0.59 (D) | Benzyl bromide: Ex. No. XXVIII<br>Heterocycle: Ex. No. VIII |
| XLI | [4-CH3, 2-CH3, N-CH3 cyclohepta-pyrido-indole] | cHept | 0.29 (H) | Benzyl bromide: Ex. No. XXX<br>Heterocycle: Ex. No. VIII |

TABLE IV-continued

[Structure: 4-(ZCH2)-phenyl-CH(D)-CO2tBu, racemic]

| Ex. No. | Z | D | R_f (solvent) | Starting material (Syn. from Ex. No.) |
|---|---|---|---|---|
| XLII | 4-CF3-2-CH3-N-methyl-tetrahydro-pyrido-indole | cPent | 0.70 (M) | Benzyl bromide: Ex. No. XXVIII<br>Heterocycle: Ex. No. IX |
| XLIII | 4-CF3-2-CH3-N-methyl-tetrahydro-pyrido-indole | cHept | 0.36 (H) | Benzyl bromide: Ex. No. XXX<br>Heterocycle: Ex. No. IX |
| XLIV | 4-CH3-N-methyl-tetrahydro-pyrido-indole | cHept | 0.48 (L) | Benzyl bromide: Ex. No. XXX |
| XLV | N-methyl-β-carboline isomer | cPent | 0.49 (C) | Benzyl bromide: Ex. No. XXVIII |
| XLVI | N-methyl-β-carboline isomer | cPent | 0.51 (C) | Benzyl bromide: Ex. No. XXVIII |
| XLVII | 3-CO2C2H5-N-methyl-β-carboline | cPent | 0.54 (C) | Benzyl bromide: Ex. No. XXVIII |
| XLVIII | 2,4-di-CH3-N-methyl-tetrahydro-pyrido-indole | cPent | 0.37 (N) | Benzyl bromide: Ex. No. XXVIII<br>Heterocycle: Ex. No. XI |

TABLE IV-continued

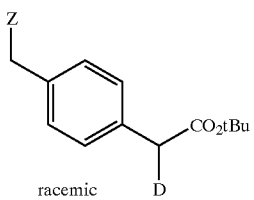

| Ex. No. | Z | D | R_f (solvent) | Starting material (Syn. from Ex. No.) |
|---|---|---|---|---|
| IL | 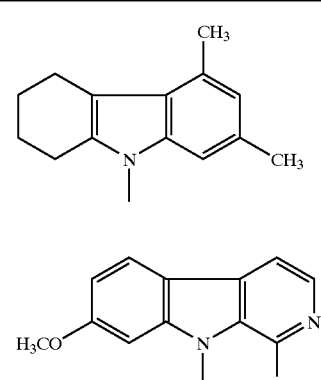 | cHept | 0.56 (H) | Benzyl bromide: Ex. No. XXX<br>Heterocucle: Ex. No. XI |
| L | 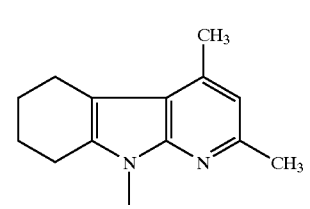 | cPent | 0.57 (C) | Benzyl bromide: Ex. No. XXVIII |
| LI | 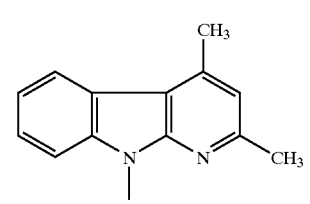 | cHex | 0.35 (H) | Benzyl bromide: Ex. No. XXIX<br>Heterocycle: Ex. No. VI |
| LII | 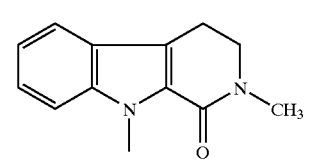 | cHex | 0.57 (B) | Benzyl bromide: Ex. No. XXIX<br>Heterocycle: Ex. No. XIX |
| LIII | 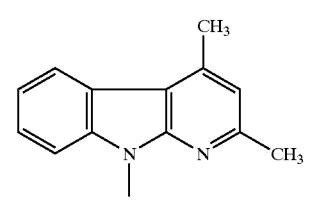 | cPent | M.p. = 189–190° C. | Benzyl bromide: Ex. No. XXVIII<br>Heterocycle:<br>a) C. Herdeis et al., Heterocycles 22, 2277 (1984). |
| LIV |  | iBu | 0.49 (M)<br>M.p.: 142° C.<br>MS (CI/NH$_3$) 457 (100%) | Benzyl bromide: c) Ex. No. XXXII<br>Heterocycle: c) Ex. No. XIX |

TABLE V

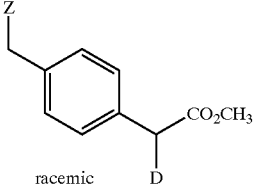

racemic

| Ex. No. | Z | D | $R_f$ (solvent) MS/M.p. | Starting material (Syn. from Ex. No.) |
|---|---|---|---|---|
| LV | 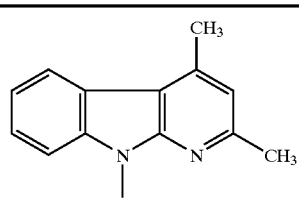 | iPr | 0.39 (M) M.p. = 159° C. MS (CI/NH$_3$): 401 (100%) | Benzyl bromide: Ex. No. XXXI Heterocycle: Ex. No. XIX |
| LVI | 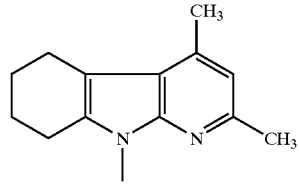 | cPent | 0.76 (B) | Benzyl bromide: Ex. No. XXXIII Heterocycle: Ex. No. XIX |
| LVII | 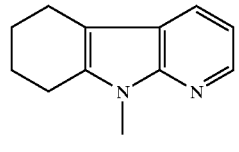 | cHept | 0.26 (H) | Benzyl bromide: Ex. No. XXXIV Heterocycle: Ex. No. VI |
| LVIII | 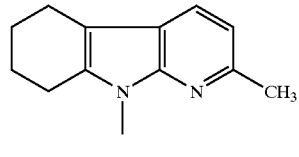 | cHept | 0.64 (K) | Benzyl bromide: Ex. No. XXXIV |
| LIX | 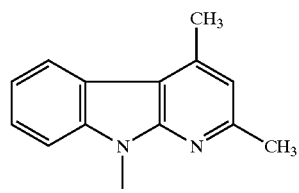 | cHept | 0.29 (H) | Benzyl bromide: Ex. No. XXXIV Heterocycle: Ex. No. X |
| LX |  | cHept | 0.30 (H) | Benzyl bromide: Ex. No. XXXIV Heterocycle: Ex. No. XIX |

EXAMPLE LXI 2-(R,S)-2-Cyclopentyl-2-[4-(2,4dimethyl-α-carbolin-9-yl)methyl]phenyl-acetic acid hydrochloride

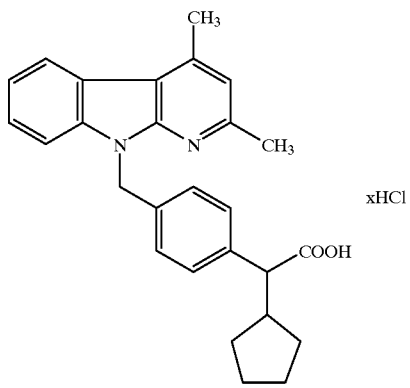

139.8 g, (298 mmol) of the compound from Example XXXV are dissolved in 1 l of 1,4dioxane and the solution is stirred at 70° C. for 3 h with 240 ml of concentrated hydrochloric acid (37% strength). After reaction is complete (TLC checking, petroleum ether: ethyl acetate=10:1), the mixture is cooled to about 15° C. and then poured in portions into 5 l of water. The pH is adjusted to 2.8 using 2 M aqueous sodium hydroxide solution, and the precipitate obtained is filtere off with suction through a paper filter and washed with water until the washing water has a pH>4. The rapidly filtered off solid is stirred with 1 I of petroleum ether (boilig range 60–80° C.), filtered off with suction again and dried over phosphorus pentoxide in vacuo.

Yield: 130.3 g (290 mmol/97%/)
M.p.: 260–262° C. (uncorrected)
$R_f$=0.51 (dichloromethane : ethanol=20: 1)
$^1$H-NMR (d$_6$-DMSO, 200 MHz, TMS): δ=0.88 (M 1 H), 1.09–1.67 (M, 6 H) 1.79 (M, 1 H), 2.38 (M, 1 H), 2.68 (S, 3 H), 2.84 (S, 3 H), 3.16 (D, 1 H), 4.7–5.9 (1 H), 5.80 (S, 2 H), 7.12–7.26 (M, 5 H), 7.32 (M, 1 H), 7.49 (M, 1 H), 7.59 (D, 1 H), 8.17 (D, 1 H) ppm The compounds of Table VI are prepared analogously to the procedure of Example LXI:

TABLE VI

| Ex. No. | Z | D | $R_f$ (solvent) | Starting material (Syn. from Ex. No.) |
|---|---|---|---|---|
| LXII | 2,4-dimethyl-5,6,7,8-tetrahydro-α-carbolin-9-yl (N-methyl) | cPent | 0.37 (A) | Ex. No. XXXVI |
| LXIII | 2,4-dimethyl-α-carbolin-9-yl (N-methyl) | cHept | 0.23 (G) | Ex. No. XXXVII |
| LXIV | 2,4-dimethyl-cyclopenta-α-carbolin-yl (N-methyl) | cHept | 0.30 (E) | Ex. No. XXXVIII |

TABLE VI-continued

[Structure: racemic 4-(Z-CH2)-phenyl-CH(D)-COOH]

| Ex. No. | Z | D | Rf (solvent) | Starting material (Syn. from Ex. No.) |
|---|---|---|---|---|
| LXV | 4,2-dimethyl-9-methyl-6,7,8,9-tetrahydro-pyrido[2,3-b]indol-3-yl (cyclohexane-fused, CH3 at 4 and 2, N-CH3) | cHept | 0.27 (D) | Ex. No. XXXIX |
| LXVI | 4,2-dimethyl-N-methyl cycloheptane-fused pyrido[2,3-b]indol-3-yl | cPent | 0.37 (C) | Ex. No. XL |
| LXVII | 4,2-dimethyl-N-methyl cycloheptane-fused pyrido[2,3-b]indol-3-yl (isomer) | cHept | 0.15 (C) | Ex. No. XLI |
| LXVIII | 4-CF3, 2-CH3, N-CH3 cyclohexane-fused pyrido[2,3-b]indol-3-yl | cPent | 0.43 (A) | Ex. No. XLII |
| LXIX | 4-CF3, 2-CH3, N-CH3 cyclohexane-fused pyrido[2,3-b]indol-3-yl | cHept | 0.27 (C) | Ex. No. XLIII |
| LXX | 4-CH3, N-CH3 cyclohexane-fused pyrido[2,3-b]indol-3-yl | cHept | 0.17 (E) | Ex. No. XLIV |
| LXXI | N-methyl-β-carboline (pyrido[3,4-b]indol) | cPent | 0.07 (C) | Ex. No. XLV |

TABLE VI-continued

[Structure: racemic compound with Z-CH2-phenyl-CH(D)-COOH]

| Ex. No. | Z | D | R_f (solvent) | Starting material (Syn. from Ex. No.) |
|---|---|---|---|---|
| LXXII | 9-methyl-β-carboline (pyrido-indole) | cPent | 0.26 (C) | Ex. No. XLVI |
| LXXIII | 9-methyl-β-carboline-3-carboxylic acid ethyl ester (CO$_2$C$_2$H$_5$) | cPent | 0.39 (C) | Ex. No. XLVII |
| LXXIV | 1,3-dimethyl-tetrahydrocarbazole (CH$_3$, CH$_3$) | cPent | 0.46 (C) | Ex. No. XLVIII |
| LXXV | 1,3-dimethyl-tetrahydrocarbazole (CH$_3$, CH$_3$) | cHept | 0.68 (E) | Ex. No. IL |
| LXXVI | 7-methoxy-1-methyl-9-methyl-β-carboline (H$_3$CO-, CH$_3$) | cPent | 0.44 (C) | Ex. No. L |
| LXXVII | 2,4-dimethyl-tetrahydro-α-carboline (CH$_3$, CH$_3$) | cHex | 0.44 (C) | Ex. No. LI |

TABLE VI-continued

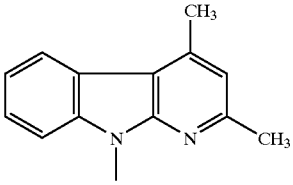

| Ex. No. | Z | D | R_f (solvent) | Starting material (Syn. from Ex. No.) |
|---|---|---|---|---|
| LXXVIII | 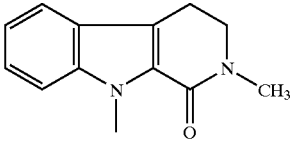 | cHex | 0.55 (C) | Ex. No. LII |
| LXXIX | 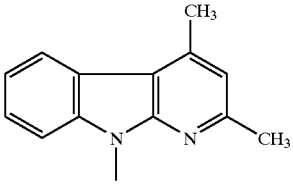 | cPent | M.p. = 204–205° C. | Ex No. LIII |
| LXXX | 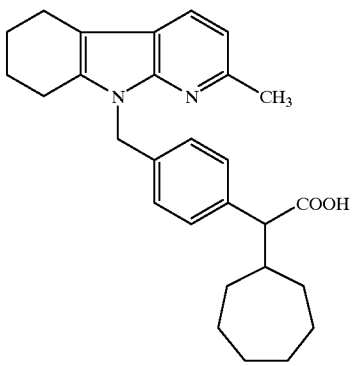 | iBu | 0.36 (A) M.p.: 156° C. MS(FAB): 401 (100%) 154 (90%) | Ex. No. LIV |

EXAMPLE LXXXI 2-(R, S)-2-[4-(2-Methyl-5,6,7, 8-tetrahydro-α-carbolin-9-yl)-methyl-phenyl]-2-cylcoheptyl-acetic acid 1.5 g (3.37 mmol) of the compound from Example LIX are reacted with 20 ml of 1 M methanolic sodium hydroxide solution for 48 h. Water is added thereto and the methanol component is evaporated. The alkaine aqueous phase is extracted several times with ether, freed from residues of organic solvent in vacuo and adjusted to a pH of about 2 at 0–5° C. using aqueous 1 M hydrochloric acid. The precipitate which is deposited in this process is filtered off with suction, thoroughly washed with water and dried over phosphorus pentoxide in a high vacuum.

Yield: 1.18 g

The reaction can be accelerated using potassium hydroxide instead of sodium hydroxide and with addition of 1. 4, 7, 10, 13, 16-hexaoxacyclooctadecane.

$R_f$=0.39 (petroleum ether : ethyl acetate=2:1)

The compounds of Table VII are prepared in analogy to the procedure of Example LXXXI:

TABLE VII
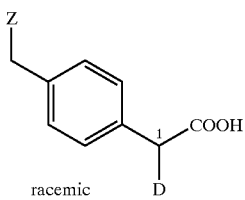
| Ex. No. | Z | D | 1 | R$_f$ (solvent) MS/M.p. | Starting material (Synthesis from Ex. No.) |
|---|---|---|---|---|---|
| LXXXII Method 1 | 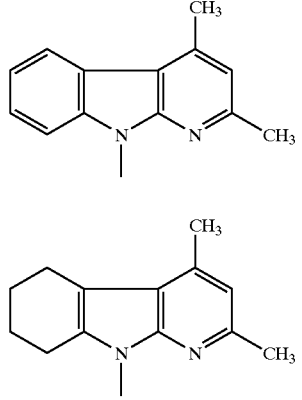 | iPr | rac | 0.28 (A) M.p. = 225° C. MS(FAB): 387 (100%) 154 (80%) | Ex. No. LV |
| LXXXIII | 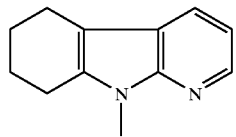 | cHept | rac | 0.05 (L) | Ex. No. LVII |
| LXXXIV | 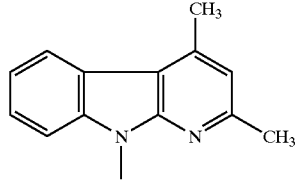 | cHept | rac | 0.11 (K) | Ex. No. LVIII |
| LXXXVI | 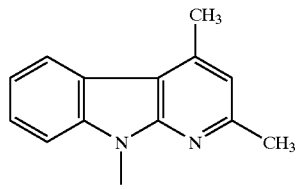 | cHept | rac | 0.23 (G) | Ex. No. LX |
| LXXXVI | 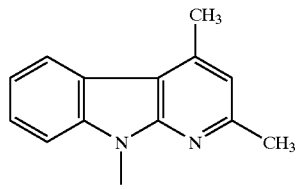 | cPent | rac | 0.51 (C) | Ex. No. LVI |

Example LXXXII can also be prepared by method 2 which follows:

2-[4(2,4Dimethyl-α-carbolin-9-yl)-methyl-phenyl]-2-(prop-2-yl)acetic acid

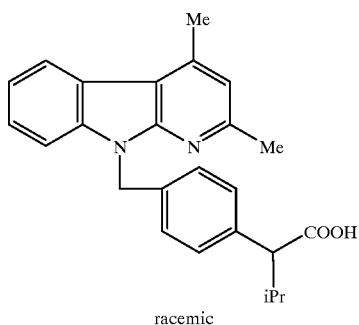

racemic 1.11 g (2.77 mmol) of the compound from Example No. LV are boiled under reflux for 18 hours in 45 ml of methanol and 3 ml of 2 M aqueous sodium hydroxide solution. As the reaction is incomplete according to TLC (dichloromethane: methanol=20: 1), 30 ml of tetrahydrofuran and a furither 3 ml of 2 M aqueous sodium hydroxide solution are added, a clear solution being obtained. After boiling under reflux for four hours, the reaction is complete (TLC, see above). The mixture is cooled, diluted with water and neutralized with 2 M aqueous hydrochloric acid. The precipitate which is obtained in this process is filtered off with suction, washed with water and dried over phosphorus pentoxide in vacuo.

Yield: 0.597 g

M.p.=225° C.

$R_f$=0.28 (dichloromethane: methanol=20:1)

The compounds of Table VIII are prepared analogously to the procedure of Example XXXV:

TABLE VIII

| Ex. No. | —Z | M.p. (° C.) | Starting material* |
| --- | --- | --- | --- |
| LXXXVII | | 164–165 | |
| LXXXVIII | | 201–202 | |

*Ex. No. XXVIII was employed as the benzyl bromide.

The compounds of Table IX are prepared analogously to the procedure of Example LXI:

TABLE IX

| Ex. No. | —Z | M.p. (° C.) | Starting material from Ex. No. |
|---|---|---|---|
| LXXXIX | | 262–263 | LXXXVII |
| XC | | 279–280 | LXXXVIII |

EXAMPLE XCI

2-Hydrazino-5-trifluoromethylpyridine

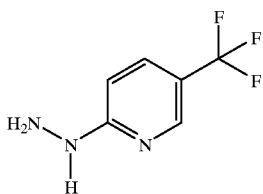

In analogy to the procedure of Example No. IV, 2-hydrazino-5-trifluoromethylpyrdine is prepared from 2-chloro-5-trifluoromethylpyridine.
$R_f$=0.37 (BABA)

EXAMPLE XCII

5-Oxo-5,6,7-tetrahydro-α-carboline

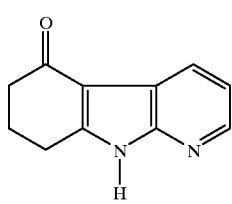

3.3 g (19.2 mmol) of 5,6,7,8-tetrahydro-α-carboline (Lit.: S. Okuda and M. M. Robinson, J. Am. Chem. Soc. 81, 740 (1959)) are initially introduced into 43 ml of tetrahydrofuran while stirring at 0° C. and the mixture is treated dropwise with a solution of 15.5 g (68.2 mmol) of DDQ in 277 ml of tetrahydrofuran and 31 ml of water. The reaction mixture is stirred at 0° C. for 5 minutes and at 20° C. for 2 hours, then treated with a buffer of pH=10 (Merck) and extracted with diethyl ether. The evaporated organic phase yields a crude product which is purified by chromatography (silica gel 60, Merck, first petroleum ether: ethyl acetate=1:1, then dichloromethane : methanol=20:1). The fractions thus obtained are precipitated by stirring with acetone, and the product is filtered off with suction and freed from the solvent in vacuo.

Yield: 0.92 g $R_f$=0.17 (petroleum ether: ethyl acetate=1:4).

The compounds of Table X are prepared analogously to the procedure of Example VI:

TABLE X

| Ex. No. | —Z— | M.p. (° C.) R$_f$ (solvent) | MS (EI) | Starting material from Ex. No. |
|---|---|---|---|---|
| XCIII | [structure: tetrahydro-pyrido-indole with Me] | 0.27 (E) | | V |
| XCIV | [structure: tetrahydro-pyrido-indole with CF$_3$] | 0.46 (G) | 240 (52%) 212 (100%) | XCI |

The compounds of Table XI are prepared analogously to the procedure of Example XIX:

TABLE XI

| Ex. No. | —Z— | M.p. (° C.) R$_f$ (solvent) | MS (EI) | Starting material from Ex. No. |
|---|---|---|---|---|
| XCV | [structure: pyrido-indole with CF$_3$ and Me] | 0.39 (G) | 250 (100%) | IX |
| XCVI | [structure: pyrido-indole with Me] | 0.45 (G) | | X |
| XCVII | [structure: pyrido-indole with CF$_3$] | 0.48 (G) | 236 (100%) | XCIV |
| XCVIII | [structure: pyrido-indole with Me] | 0.3 (E) | | XCIII |

The compounds of Table XII are prepared analogously to the procedure of Example XXXV:

TABLE XII

[Structure: Z-CH2-C6H4-CH(D)(CO2tBu), *racemic]

| Ex. No. | Z | D | M.p. [° C.] Rf (solvent) | Starting material from Ex. No. |
|---|---|---|---|---|
| IC | [tetrahydro-pyrido-indole] | cPent | 0.73 (C) | Benzyl bromide: Ex. No. XXVIII |
| C | [pyrido-indole with CF3 and Me] | cPent | 0.63 (H) | Benzyl bromide: Ex. No. XXVIII; Heterocycle: Ex. No. XCV |
| CI | [pyrido-indole with Me] | cPent | 0.27 (H) | Benzyl bromide: Ex. No. XXVIII; Heterocycle: Ex. No. XCVI |
| CII | [tetrahydro-pyrido-indole with CF3] | cPent | 0.33 (H) | Benzyl bromide: Ex. No. XXVIII; Heterocycle: Ex. No. XCI |
| CIII | [pyrido-indole with CF3] | cPent | 0.41 (H) | Benzyl bromide: Ex. No. XXVIII; Heterocycle: Ex. No. XCVII |
| CIV | [pyrido-indole with Me] | cPent | 0.18 (H) | Benzyl bromide: Ex. No. XXVIII; Heterocycle: Ex. No. XCVIII |

The compounds of Table XIII are prepared analogously to the procedure of Example LXI:

TABLE XIII

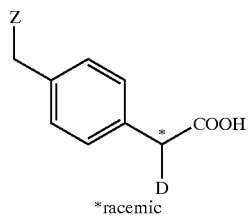
*racemic

| Ex. No. | Z | D | M.p. [° C.] R_f (solvent) | Starting material from Ex. No. |
|---|---|---|---|---|
| CV | (tetrahydro-pyrido-indole) | cPent | 0.27 (C) | IC |
| CVI | (pyrido-indole with CF_3 and Me) | cPent | 0.49 (C) | C |
| CVII | (pyrido-indole with Me) | cPent | 0.38 (C) | CI |
| CVIII | (tetrahydro-pyrido-indole with CF_3) | cPent | 0.35 (C) | CII |
| CIX | (pyrido-indole with CF_3) | cPent | 0.43 (C) | CIII |
| CX | (pyrido-indole with Me) | cPent | 0.29 (C) | CIV |

EXAMPLE NO. CXI 1-(R,S)-1-Phenyl-2-triphenylmethyloxy-ethanol

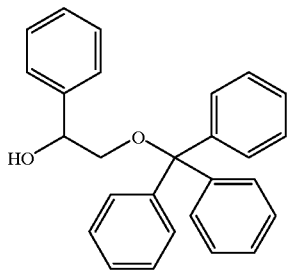

13 g (94 mmol) of 1(R,S)-1-Phenyl-2-hydroxy-ethanol are reacted at 20° C. with 15.6 ml (113 mmol) of trietiylamine and 23.6 g (84.6 mmol) of triphenylmethyl chloride in 200 ml of DNF. After 20 h, the mixture is poured into buffer of pH=4 (Merck), the phases are separated, and the organic phase is dried with magnesium sulphate and evaporated to dryness. The crude product is purified by chromatography on silica gel 60 (Merck/petroleum ether:ethyl acetate=20:1 later 10:1); yield 27 g.

$R_f$=0.36 (petroleum ether: ethyl acetate=5:1)

EXAMPLE NO. CXII

6-Chloro-5-methyl-3-nitro-2-(2-oxo-cyclohexyl)-pyridine

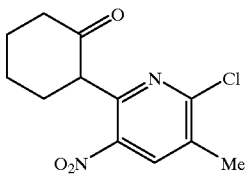

20 g (95.7 mmol) of 2,6-dichloro-5-methyl-3-nitro-pyridine are reacted with 13.3 ml (95.7 mmol) of triethylamine and 14.5 g (95.7 mmol) of freshly distilled 1-pyrrolidino-cyclopentene at 20° C. in 200 ml of DMF under argon as a protective gas. After the starting material has disappeared according to thin-layer chromatography (silica gel/petroleum ether: ethyl acetate=4:1), 200 ml of 1 M hydrochloric acid are added and the mixture is diluted with about 600 ml of water. The precipitate which is deposited is filtered off with suction, dried over phosphonrs pentoxide in a high vacuum and purified by chromatography (silica gel 60/Merck/petroleum ether: ethyl acetate=2:1). $R_f$=0.69 (petroleum ether: ethyl acetate=4:1)

EXAMPLE NO. CXIII

2-Methyl-5,6,7,8-tetrahydro-δ-carboline

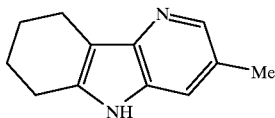

2.8 g (10.4 mmol) of the compound from Example CXII are reacted on 0.5 g of palladium (5%) / carbon in 30 ml of THF under a hydrogen pressure of 3 bar for 18 h. The catalyst is then filtered off with suction and washed several times with methanol and dichloromethane. The filtrate is evaporated and dried in a high vacuum; yield: 2.1 g
$R_f$=0.53 (dichloromethane: ethanol=5:1)

EXAMPLE NO. CXIV

3-Methyl-5,6,7,8-tetrahydro-α-carboline hydrochloride

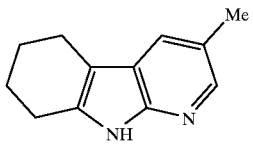

13.0 g (120.2 mmol) of 2-amino-5-methyl-pyridine are dissolved in 150 ml of ethanol and the solution is stirred with 60 ml of 2 M hydrochloric acid, evaporated to dryness and finally dried over sodium hydroxide and phosphorus pentoxide in a high vacuum. The product thus obtained is boiled under reflux in a water separator with 2.2 g (20.1 mmol) of 2-amino-5-methyl-pyridine and 11.4 g (50.0 mmol) of 2-hydroxy-cyclohexanone dimer in 120 ml of 1,2-dichlorobenzene for 6 h. 1 11.4 g (50.0 mmol) of 2-hydroxy-cyclohexanone dimer are then added again and the mixtue is boiled under reflux for a further 3 h. On cooling, a precipitate is deposited at 20° C. 150 ml of acetone are added, the mixture is cooled to 0 to 5° C. with stiring, and the precipitate is filtered off with suction and washed with cold ether. The product obtained is dried over phosphorus pentoxide in a high vacuum; yield 18 g.
$R_f$=0.29 (dichloromethane: ethanol=20:1)

The compounds of the following Table XIV are obtained in analogy to the procedure of Example No. XIX:

TABLE XIV

| Ex. No. | Heterocycle | $R_f$ (solvent) | Starting material |
|---|---|---|---|
| CXV | 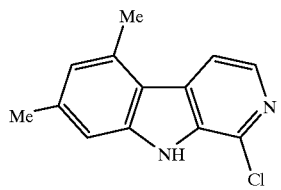 | 0.16 (C) | |
| CXVI | | 0.37 (C) | Ex. No. CXIII |
| CXVII | | 0.17 (D) | Ex. No. CXIV |

EXAMPLE NO. CXVIII

1-Chloro-5,7-dimethyl-β-carboline

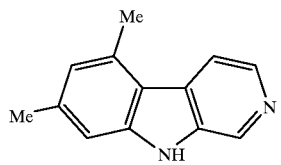

10.2 g (49 mmol) of the compound from Example No. CXV are reacted at 125° C. for 24 h with 222 ml (2.4 mol) of phosphorus oxychloride and 155 µl of N,N-dimethyl-aniline. The mixture is poured into 1 l of ice water after cooling, then neutralized with aqueous sodium carbonate solution and exited several times with ethyl acetate. The organic phase is dried with magnesium sulphate, evaporated and freed from the residual solvent in a high vacuum. The crude product is purified by chromatography on silica gel 60 (Merck/dichloromethane);
yield: 4.3 g.
$R_f$=0.39 (dichloromethane: ethanol=20:1)

EXAMPLE NO. CXIX 5,7-Dimethyl-β-carboline 3.8 g (16.5 mmol) of the compound from Example CXVIII are reacted with 1.3 g of sodium hydrogen carbonate on 700 mg of palladium (10%)/carbon at a hydrogen pressure of about 3 bar and 20° C. for 10 d in 40 ml of THF, 300 mg of palladium (10%)/carbon and 5 ml of methanol being added on every second day. The catalyst is then filtered off with suction through kieselguhr, washed with THF, boiled in methanol and dichloromethane and again filtered off with suction. The combined organic solutions are evaporated, and the residue is precipitated by stirring with ether and filtered off with suction. After vacuum drying, 3 g of product are obtained.

$R_f$=0.13 (dichloromethane: ethanol=20:1)

EXAMPLE NO. CXX 5,6-Dimethyl-1-(pyrid-2-yl)-1 H-benzotriazole

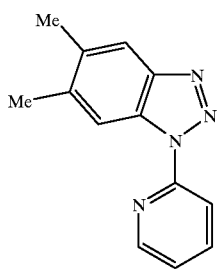

14.85 g (103 mmol) of 5,6dimethyl-1 H-benzotriazole are dissolved in 150 ml of anhydrous DMSO, reacted with 5 g (104 mnuol) of 50% strength sodium hydride (+40% paraffin oil) at 20° C. until evolution of hydrogen is complete, treated with 10 g (103 mmol) of 2-fluoro-pyridine and the mixture is boiled under reflux for 18 h. After cooling to 20° C., the mixture is made up to a volume of about 1 l with water, and the resulting precipitate is filtered off with suction and washed with water. The substance, which is dried over phosphorus pentoxide in a high vacuum, is purified by chromatography on silica gel 60 (Merck/dichloromethane to dichloromethane: ethanol=100:1);
yield: 10.6 g.
$R_f$=0.38 (dichloromethane: ethanol=50:1)

EXAMPLE NO. CXXI 6,7-Dimethyl-α-carboline

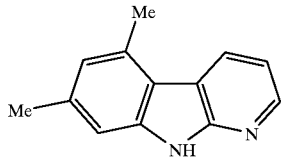

8.9 g (39.7 mmol) of the compound from Example No. CXX are slowly heated to 165° C. in 140 g of polyphosphoric acid under argon, the mixture being poured into 1.5 l of water and adjusted to pH=6–7 with 1 M aqueous sodium hydroxide solution before disappearance of the starting material (TLC checking/dichioromethane: ethanol=20:1). The precipitate obtained is filtered off with suction, washed with water, rapidly filtered off with suction, then washed with petroleum ether and filtered off with suction again. After vacuum drying, 1.8 g of product are obtained.
$R_f$=0.32 (dichloromethane: ethanol=20:1)

The compounds in Table XV are prepared in analogy to the procedure of Example No. XXI:

TABLE XV

| Ex. No. | | $R_f$ (solvent) |
|---|---|---|
| CXXII | (3-methylphenyl-cyclopentyl-acetic acid methyl ester) | 0.56 (H) |
| CXXIII | (4-methylphenyl-(3,3-dimethylbutyl... ethyl ester structure) | |
| CXXIV | (4-methylphenyl-heptyl acetic acid tert-butyl ester) | |

The compounds in Table XVI are prepared in analogy to the procedure of Example No. XXVIII:

TABLE XVI

| Ex. No. | | $R_f$ (solvent) | Starting material (Ex. No.) |
|---|---|---|---|
| CXXV | (3-bromomethylphenyl-cyclopentyl-acetic acid methyl ester) | 0.40 (H) | CXXII |
| CXXVI | (4-bromomethylphenyl-... ethyl ester structure) | | CXXIII |

TABLE XVI-continued

| Ex. No. | | $R_f$ (solvent) | Starting material (Ex. No.) |
|---|---|---|---|
| CXXVII | 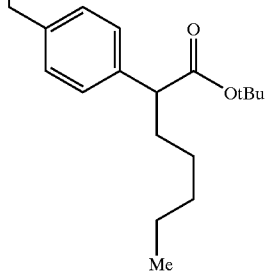 | | CXXIV |

The compounds of Table XVII are prepared analogously to the procedure of Example No. XXXV:

TABLE XVII

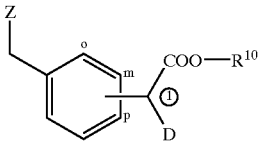

| Ex. No. | Z | Position (o, m or p) | î | D | $R^{10}$ | $R_f$ (solvent) | MS | Starting material Ex. No. |
|---|---|---|---|---|---|---|---|---|
| CXXVIII | 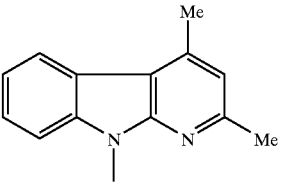 | p | — | H | Me | 0.59 (G) | DCI: 359 (100%) | XIX |
| CXXIX | 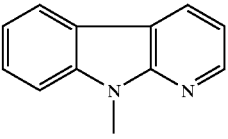 | p | rac | cPent | Me | 0.51 (D) | | XXXIII |
| CXXX | 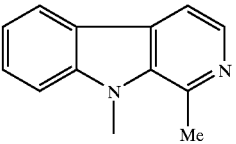 | p | rac | cPent | Me | 0.22 (C) | | XXXIII (Harman is commercially available from Aldrich). |
| CXXXI | 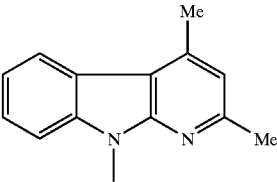 | m | rac | cPent | Me | 0.55 (D) | | XIX and CXXV |

TABLE XVII-continued

| Ex. No. | Z | Position (o, m or p) | î | D | R[10] | R_f (solvent) | MS | Starting material Ex. No. |
|---|---|---|---|---|---|---|---|---|
| CXXXII | [4-Me-β-carboline N-Me, pyridine N at 5-position] | p | | rac cPent | Me | 0.21 (D) | | CXVI and XXXIII |
| CXXXIII | [6,7-diMe-α-carboline N-Me] | p | | rac cPent | tBu | | | XXVIII and CXXI |
| CXXXIV | [3-Me-α-carboline N-Me] | p | | rac cPent | tBu | | | XXVIII and CXVII |
| CXXXV | [5,7-diMe-γ-carboline N-Me] | p | | rac cPent | tBu | | | XXVIII and CXIX |
| CXXXVI | [1,3-diMe-β-carboline N-Me] | p | | rac cPent | Me | 0.13 (L) | | XXXIII |
| CXXXVII | [2,4-diMe-α-carboline N-Me] | p | | rac Me | tBu | 0.43 (L) | | XIX |
| CXXXVIII | [2,4-diMe-α-carboline N-Me] | p | | rac Et | tBu | 0.51 (L) | | XIX |

TABLE XVII-continued

[Structure: Z-CH2-phenyl(o,m,p)-C(D)(COO-R^10)]

| Ex. No. | Z | Position (o, m or p) | ① | D | R^10 | R_f (solvent) | MS | Starting material Ex. No. |
|---------|---|----------------------|---|---|------|---------------|-----|---------------------------|
| CXXXIX | 4-Me, 2-Me, N-Me α-carboline | p | rac | nPent | Et | | | XIX and CXXVII |
| CXL | 4-Me, 2-Me, N-Me α-carboline | p | rac | CH(Me)(CH2Me) i.e. sec-Bu | Et | | | XIX and CXXVI |

The compounds of Table XVIII are prepared analogously to the procedure of Example Nos. LXI or LXXXI:

TABLE XVIII

[Structure: Z-CH2-phenyl(o,m,p)-C(D)(COOH)]

| Ex. No. | Z | Position (o, m or p) | ① | D | R_f (solvent) | MS | Starting material Ex. No. | Preparation analogous to Ex. No. |
|---------|---|----------------------|---|---|---------------|-----|--------------------------|----------------------------------|
| CXLI | 4-Me, 2-Me, N-Me α-carboline | p | — | H | 0.56 (O) | | CXXVIII | LXXXI |
| CXLII | N-Me α-carboline | p | rac | cPent | 0.14 (G) | | CXXIX | LXXXI |
| CXLIII | 1-Me, N-Me β-carboline | p | rac | cPent | 0.50 (U) | | CXXX | LXXXI |

TABLE XVIII-continued

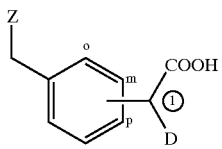

| Ex. No. | Z | Position (o, m or p) | ① | D | R$_f$ (solvent) | MS | Starting material Ex. No. | Preparation analogous to Ex. No. |
|---|---|---|---|---|---|---|---|---|
| CXLIV | [4-Me, 2-Me pyrido-indole, N-Me] | m | rac | cPent | 0.14 (D) | | CXXXI | LXXXI |
| CVL | [3-Me pyrido-indole, N-Me] | p | rac | cPent | 0.10 (D) | | CXXXII | LXXXI |
| CVLI | [6,7-diMe pyrido-indole, N-Me] | p | rac | cPent | 0.34 (C) | | CXXXIII | LXI |
| CVLII | [3-Me pyrido-indole, N-Me] | p | rac | cPent | | | CXXXV | LXI |
| CVLIII | [5,7-diMe pyrido-indole, N-Me] | p | rac | cPent | 0.15 (C) | | CXXXV | LXI |
| CIL | [1-Me, 3-Me pyrido-indole, N-Me] | p | rac | cPent | | | CXXXVI | LXXXI |
| CL | [4-Me, 2-Me pyrido-indole, N-Me] | p | rac | Et | | | CXXXVIII | LXI |

TABLE XVIII-continued

Structure: Z-CH2-[phenyl ring with positions o, m, p]-C(①)(D)(COOH)

| Ex. No. | Z | Position (o, m or p) | ① | D | R_f (solvent) | MS | Starting material Ex. No. | Preparation analogous to Ex. No. |
|---|---|---|---|---|---|---|---|---|
| CLI | 2,4-dimethyl-α-carboline-9-yl-methyl (Me at 4, Me at 2) | p | rac | Me | | | CXXXVII | LXI |
| CLII | 2,4-dimethyl-α-carboline-9-yl-methyl | p | rac | nPent | | | CXXXIX | LXXXI |
| CLIII | 2,4-dimethyl-α-carboline-9-yl-methyl | p | rac | CH(Me)Me | | | CXL | LXXXI |

PREPARATION EXAMPLES

EXAMPLES 1, 2 and 3

2-(S)- and 2-(R)-2-[4-(2,4-Dimethyl-5,6,7,8-tetrahydro-α-carbolin-9-yl)methyl-phenyl]-2-cyclopentyl-acetic acid N-[(R)phenylglycinolamide]

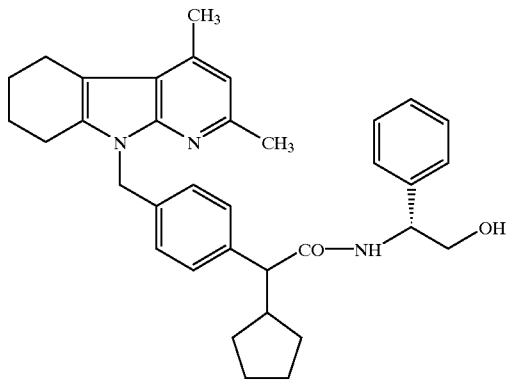

3.00 g (7.2 mmol of the compound from Example LXII are dissolved in 70 ml of dichloromethae with 0.99 g (7.2 mmol) of (R)-phenylglycinol (Aldrich), and the solution is treated successively at 0° C. with 1.07 g (7.9 mmol) of 1-hydroxy-1 H-* benztriazole hydrate (Aldrich), 1.58 g (8.3 mmol) of N'-(3-dimethylaniiopropyl)-N-ethycabodiimide hydrochloride (Aldrich) and 2 ml of triethylamine and then stirred at room temperature for 20 hours. The organc solution is extracted with aqueous ammonium chloride solution, with aqueous sodium hydrogen carbonate solution and with a buffer of pH=4 (ready-touse buffer solution, E. Merck, Darmstadt), dried with solid anhydrous sodium sulphate and evaporated.

Yield of the diastereomer mixture: 3.50 g (Example 1).

The product mixture is separated by chromatograhy (silica gel, dichloromethane: ethanol 50:1):

EXAMPLE NO. 2

Diastereomer A [2(S)-diastereomer]: 1.23 g
$R_f$=0.18 (dichloromethane: ethanol=50: 1)
$^1$H-NMR (d-DMSO, 250 MHz, TMS):δ=0.87 (M, 1 H), 1.19–1.63 (M, 6 H), 1.72 (M, 1 H), 2.45 (M, 1 H), 2.58 (S, 3 H), 2.79 (S, 3 H), 3.26 (D, 1 H), 3.44–3.53 (M, 2 H), 4.21–4.31 (M, 2 H), 5.63 (S, 2 H), 6.97–7.11 (M, 8 H), 7.20–7.28 (M, 3 H), 7.41 (M, 1 H), 7.54 (D, 1 H), 8.12 (D, 1 H), 8.24 (D, 1 H) ppm.

EXAMPLE NO. 3

Diastereomer B [2(R)-diastereomer]: 1.12 g
$R_f$=0.16 (dichloromethane: ethanol=50:1)
$^1$H-NMR (d-DMSO, 250 MHz, TMS): δ=0.84 (M, 1 H), 1.07–1.59 (M, 7 H), 2.34 (M, 1 H), 2.61 (S, 3 H), 2.80 (S, 3 H), 3.25 (D, 1 H), 3.43 (M, 2 H), 4.63–4.72 (M, 2 H), 5.66 (S, 2 H), 6.98 (S, 1 H), 7.13 (M, 2 H), 7.20–7.30 (M, 8 H), 7.43 (M, 1 H), 7.57 (D, 1 H), 8.12 (D, 1 H), 8.36 (D, 1 H) ppm.

The absolute configurations of the enantiomerically pure carboxylic acids 2-(S)- and 2-(R)-2-{4[(quinolin-2-yl)

methoxy]phenyl}-2-cyclopentyl-acetic acid [cf. EP 509 359] are known, so the absolute configurations of the amides Ex. No. C1 and Ex. No. C2 prepared therefrom analogously to the procedure of Examples 1 and 2 can be derived. The $^1$H-NMR spectra of the two diastereomeric products (200 MHz, $d_6$-DMSO, TMS for Example No. C1 and 250 MHz, $d_6$-DMSO, TMS for Example No. C2/FIG. 1) have significant differences in the aromatic region: the H signals of the phenyl radical of Ex. No. C1 are at about 7.1 ppm (3 H) and 7.3 ppm (2 H and the H signals of Ex. No. C2 are at about 7.3 ppm (5 H). This finding is applicable to the compounds of Examples 2 and 3 (FIG. 2) and also to many other derivatives of this type.

The examples mentioned in Tables 1, 2 and 3 are prepared in analogy to the procedure of Examples 1, 2 and 3:

TABLE 1

[Structure: Z-CH₂-(phenyl)-CH(D)-C(=O)-NH-CH(phenyl)-CH₂-OH, position 1 marked]

| Ex. No. | Z | D | 1 | $R_f$ (solvent) | Starting material *(Ex. No.) |
|---|---|---|---|---|---|
| 4 | 4-methyl-1-methyl-2-methyl-pyrido[2,3-b]indole (CH₃ at 4, CH₃ at 2, N-CH₃) | cPent | rac | 0.41/0.46 (E) | LXI |
| 5 | same as 4 | cPent | S | 0.46 (E) | LXI |
| 6 | same as 4 | cPent | R | 0.41 (E) | LXI |
| 7 | same as 4 | cHept | rac | 0.26/0.29 (D) | LXIII |
| 8 | same as 4 | cHept | S | 0.29 (D) | LXIII |

TABLE 1-continued

| Ex. No. | Z | D | 1 | $R_f$ (solvent) | Starting material *(Ex. No.) |
|---|---|---|---|---|---|
| 9 | 2,4-dimethyl-9-methyl-9H-pyrido[2,3-b]indole | cHept | R | 0.26 (D) | LXIII |
| 10 | 2,4-dimethyl-8-methyl-1,2,3,8-tetrahydro-cyclopenta[b]pyrrolo[2,3-b]pyridine | cHept | rac | 0.20/0.24 (E) | LXIV |
| 11 | 2,4-dimethyl-8-methyl-1,2,3,8-tetrahydro-cyclopenta[b]pyrrolo[2,3-b]pyridine | cHept | S | 0.24 (E) | LXIV |
| 12 | 2,4-dimethyl-8-methyl-1,2,3,8-tetrahydro-cyclopenta[b]pyrrolo[2,3-b]pyridine | cHept | R | 0.20 (E) | LXIV |
| 13 | 2,4-dimethyl-9-methyl-2,3,4,9-tetrahydro-1H-pyrido[2,3-b]indole | cHept | rac | 0.35 (C) | LXV |
| 14 | 2,4-dimethyl-9-methyl-2,3,4,9-tetrahydro-1H-pyrido[2,3-b]indole | cHept | S | 0.35 (C) | LXV |

TABLE 1-continued

| Ex. No. | Z | D | 1 | R$_f$ (solvent) | Starting material *(Ex. No.) |
|---|---|---|---|---|---|
| 15 | 2,4-dimethyl-5,6,7,8-tetrahydro-9-methyl-pyrido[2,3-b]indole | cHept | R | 0.35 (C) | LXV |
| 16 | 2,4-dimethyl-9-methyl-6,7,8,9-tetrahydro-5H-cyclohepta[b]pyrido[2,3-d]indole | cPent | rac | 0.33/0.37 (C) | LXVI |
| 17 | 2,4-dimethyl-9-methyl-6,7,8,9-tetrahydro-5H-cyclohepta[b]pyrido[2,3-d]indole | cHept | rac | 0.25/0.38 (C) | LXVII |
| 18 | 2,4-dimethyl-9-methyl-6,7,8,9-tetrahydro-5H-cyclohepta[b]pyrido[2,3-d]indole | cHept | S | 0.38 (C) | LXVII |
| 19 | 2,4-dimethyl-9-methyl-6,7,8,9-tetrahydro-5H-cyclohepta[b]pyrido[2,3-d]indole | cHept | R | 0.25 (C) | LXVII |
| 20 | 2-methyl-4-trifluoromethyl-5,6,7,8-tetrahydro-9-methyl-pyrido[2,3-b]indole | cPent | rac | 0.29 (A) | LXVIII |

TABLE 1-continued

| Ex. No. | Z | D | 1 | $R_f$ (solvent) | Starting material *(Ex. No.) |
|---|---|---|---|---|---|
| 21 | 4-CF₃, 2-CH₃, N-methyl-tetrahydro-pyrrolo[2,3-b]pyridine | cHept | rac | 0.23/0.28 (D) | LXIX |
| 22 | 4-CF₃, 2-CH₃, N-methyl-tetrahydro-pyrrolo[2,3-b]pyridine | cHept | S | 0.28 (D) | LXIX |
| 23 | 4-CF₃, 2-CH₃, N-methyl-tetrahydro-pyrrolo[2,3-b]pyridine | cHept | R | 0.23 (D) | LXIX |
| 24 | 4-CH₃, N-methyl-tetrahydro-pyrrolo[2,3-b]pyridine | cHept | rac | 0.10/0.18 (E) | LXX |
| 25 | 4-CH₃, N-methyl-tetrahydro-pyrrolo[2,3-b]pyridine | cHept | S | 0.18 (E) | LXX |
| 26 | 4-CH₃, N-methyl-tetrahydro-pyrrolo[2,3-b]pyridine | cHept | R | 0.10 (E) | LXX |
| 27 | 2-CH₃, N-methyl-tetrahydro-pyrrolo[2,3-b]pyridine | cHept | rac | 0.17/0.23 (B) | LXXXI |

TABLE 1-continued

| Ex. No. | Z | D | 1 | $R_f$ (solvent) | Starting material *(Ex. No.) |
|---|---|---|---|---|---|
| 28 | (1,2,3,4-tetrahydro-9H-pyrido[2,3-b]indol-9-yl, N-methyl) | cHept | rac | 0.12/0.15 (B) | LXXXIV |
| 29 | (9H-pyrido[3,4-b]indol-9-yl, N-methyl) | cPent | rac | 0.28 (E) | LXXI |
| 30 | (9H-pyrido[3,2-b]indol-9-yl, N-methyl) | cPent | rac | 0.29 (C) | LXXII |
| 31 | (3-CO$_2$C$_2$H$_5$ dihydro-β-carboline, N-methyl) | cPent | rac | 0.24 (C) | LXXIII |
| 32 | (2,4-dimethyl-1,2,3,4-tetrahydrocarbazole, N-methyl) | cPent | rac | 0.39/0.48 (C) | LXXIV |
| 33 | (2,4-dimethyl-1,2,3,4-tetrahydrocarbazole, N-methyl) | cPent | S | 0.48 (C) | LXXIV |
| 34 | (2,4-dimethyl-1,2,3,4-tetrahydrocarbazole, N-methyl) | cPent | R | 0.39 (C) | LXXIV |

TABLE 1-continued

| Ex. No. | Z | D | 1 | R$_f$ (solvent) | Starting material *(Ex. No.) |
|---|---|---|---|---|---|
| 35 | 1,2,4-trimethyl-tetrahydrocarbazole | cHept | rac | 0.23/0.29 (D) | LXXV |
| 36 | 7-methoxy-1-methyl-β-carboline | cPent | rac | 0.26 (A) | LXXVI |
| 37 | 2,4,9-trimethyl-tetrahydro-α-carboline | cHex | rac | 0.28/0.30 (D) | LXXVII |
| 38 | 2,4,9-trimethyl-α-carboline | cHex | rac | 0.21/0.23 (D) | LXXVIII |

*(R)-Phenylglycinol is commercially available from Aldrich.

TABLE 2

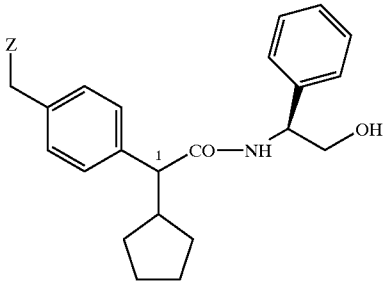

| Ex. No. | 1 | $R_f$ (solvent) | Starting material *(Ex. No.) |
|---|---|---|---|
| 39 | (structure: 1,2,4-trimethyl-pyrido-indole) | rac | 0.42 (C) | LXI |
| 40 | (structure: 1,2,4-trimethyl-pyrido-indole) | R | 0.42 (C) | LXI |
| 41 | (structure: 1,2,4-trimethyl-pyrido-indole) | S | 0.42 (C) | LXI |

*(S)-Phenylglycinol is commercially available from Aldrich.

TABLE 3

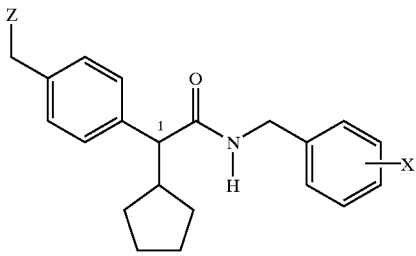

| Ex. No. | Z | D | X | 1 | $R_f$ (solvent) | Starting material (Ex. No.) |
|---|---|---|---|---|---|---|
| 42 | (1,2,4-trimethyl-pyrido-indole) | cHept | H | rac | 0.39 (C) | Carboxylic acid: Ex. No. LXIII Amine from Aldrich |

TABLE 3-continued

| Ex. No. | Z | D | X | 1 | R_f (solvent) | Starting material (Ex. No.) |
|---|---|---|---|---|---|---|
| 43 | [4,2-dimethyl cyclopenta-fused pyrrolo-pyridine, N-CH3] | cHept | H | rac | 0.78 (E) | Carboxylic acid: Ex. No. LXIV Amine from Aldrich |
| 44 | [4,2-dimethyl tetrahydro pyrido-indole, N-CH3] | cPent | H | rac | 0.34 (D) | Carboxylic acid: Ex. No. LXII Amine from Aldrich |
| 45 | [4,2-dimethyl tetrahydro pyrido-indole, N-CH3] | cPent | H | (−)-ent* | 0.34 (D) | Carboxylic acid: Ex. No. LXII Amine from Aldrich |
| 46 | [4,2-dimethyl tetrahydro pyrido-indole, N-CH3] | cPent | H | (+)-ent* | 0.34 (D) | Carboxylic acid: Ex. No. LXII Amine from Aldrich |
| 47 | [4,2-dimethyl tetrahydro pyrido-indole, N-CH3] | cHept | H | rac | 0.25 (C) | Carboxylic acid: Ex. No. LXV Amine from Aldrich |
| 48 | [4,2-dimethyl cycloheptane-fused pyrrolo-pyridine, N-CH3] | cHept | H | rac | 0.42 (C) | Carboxylic acid: Ex. No. LXVII Amine from Aldrich |

TABLE 3-continued

| Ex. No. | Z | D | X | 1 | R_f (solvent) | Starting material (Ex. No.) |
|---|---|---|---|---|---|---|
| 49 | 4-CF₃, 2-CH₃ tetrahydro-pyrido-indole | cHept | H | rac | 0.45 (C) | Carboxylic acid: Ex. No. LXIX Amine from Aldrich |
| 50 | 4-CH₃ tetrahydro-pyrido-indole | cHept | H | rac | 0.71 (E) | Carboxylic acid: Ex. No. LXX Amine from Aldrich |
| 51 | 2-CH₃ tetrahydro-pyrido-indole | cHept | H | rac | 0.59 (B) | Carboxylic acid: Ex. No. LXXXI Amine from Aldrich |
| 52 | tetrahydro-pyrido-indole | cHept | H | rac | 0.40 (B) | Carboxylic acid: Ex. No. LXXXIV Amine from Aldrich |
| 53 | 4-CH₃, 2-CH₃ tetrahydro-pyrido-indole | cHept | 3-OH | rac | 0.45 (D) | Carboxylic acid: Ex. No. LXV Amine Ref.: US 43 88 250 |
| 54 | 4-CH₃, 2-CH₃ tetrahydro-pyrido-indole | cHept | 4-OH | rac | 0.39 (A) | Carboxylic acid: Ex. No. LXV Amine: Ref.: C. Hartmann and J.P. Klinman, Biochemistry, 30, 4605 (1991) |
| 55 | 4-CH₃, 2-CH₃ tetrahydro-pyrido-indole | cHept | 2-OCH₃ | rac | 0.15 (B) | Carboxylic acid: Ex. No. LXV Amine from Aldrich |

TABLE 3-continued

| Ex. No. | Z | D | X | 1 | R_f (solvent) | Starting material (Ex. No.) |
|---|---|---|---|---|---|---|
| 56 | 2,4-dimethyl-9-methyl-6,7,8,9-tetrahydro-pyrido[2,3-b]indole | cHept | 3-OCH$_3$ | rac | 0.37 (D) | Carboxylic acid: Ex. No. LXV Amine from Lancaster |
| 57 | 2,4-dimethyl-9-methyl-6,7,8,9-tetrahydro-pyrido[2,3-b]indole | cHept | 4-OCH$_3$ | rac | 0.24 (B) | Carboxylic acid: Ex. No. LXV Amine from Aldrich |
| 58 | 2,4-dimethyl-9-methyl-6,7,8,9-tetrahydro-pyrido[2,3-b]indole | cHept | 2-O—CH$_2$—CH=CH$_2$ | rac | 0.51 (C) | Carboxylic acid: Ex. No. LXV Amine: Ex. No. II |
| 59 | 2,4-dimethyl-9-methyl-6,7,8,9-tetrahydro-pyrido[2,3-b]indole | cHept | 3-CO$_2$CH$_3$ | rac | 0.73 (C) | Carboxylic acid: Ex. No. LXV Amine: Ref. F.M. Markwardt et al., Pharmazie 22, 465 (1967). |
| 60 | 2,4-dimethyl-9-methyl-6,7,8,9-tetrahydro-pyrido[2,3-b]indole | cHept | 4-CO$_2$CH$_3$ | rac | 0.33 (B) | Carboxylic acid: Ex. No. LXV Amine: Ref.: M.G. Nair and C.M. Baugh, J. Org. Chem. 38, 2185 (1973). |
| 61 | 2,4-dimethyl-9-methyl-6,7,8,9-tetrahydro-pyrido[2,3-b]indole | cHept | 3-CH$_3$ | rac | 0.19 (B) | Carboxylic acid: Ex. No. LXV Amine from Aldrich |

TABLE 3-continued

| Ex. No. | Z | D | X | 1 | R$_f$ (solvent) | Starting material (Ex. No.) |
|---|---|---|---|---|---|---|
| 62 | 4,2-dimethyl-N-methyl-tetrahydro-α-carboline | cHept | 2-NO$_2$ | rac | 0.39 (B) | Carboxylic acid: Ex. No. LXV Amine: Ref.: EP 373 891 |
| 63 | 4,2-dimethyl-N-methyl-tetrahydro-α-carboline | cHept | 3-NO$_2$ | rac | 0.28 (B) | Carboxylic acid: Ex. No. LXV Amine from Aldrich |
| 64 | 4,2-dimethyl-N-methyl-tetrahydro-α-carboline | cHept | 4-NO$_2$ | rac | 0.21 (B) | Carboxylic acid: Ex. No. LXV Amine from Aldrich |
| 65 | 4,2-dimethyl-N-methyl-tetrahydro-α-carboline | cHept | 2-Cl | rac | 0.75 (D) | Carboxylic acid: Ex. No. LXV Amine from Aldrich |
| 66 | 4,2-dimethyl-N-methyl-tetrahydro-α-carboline | cHept | 3-Cl | rac | 0.71 (D) | Carboxylic acid: Ex. No. LXV Amine from Lancaster |
| 67 | 4,2-dimethyl-N-methyl-tetrahydro-α-carboline | cHept | 4-Cl | rac | 0.61 (D) | Carboxylic acid: Ex. No. LXV Amine from Aldrich |

TABLE 3-continued

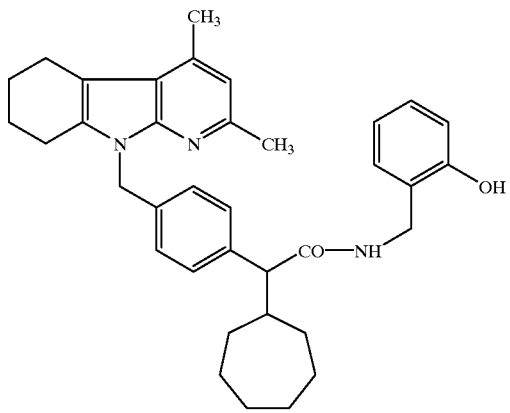

| Ex. No. | Z | D | X | 1 | $R_f$ (solvent) | Starting material (Ex. No.) |
|---|---|---|---|---|---|---|
| 68 | [4,8-dimethyl-α-carboline] | cPent | H | rac | 0.28 (D) | Carboxylic acid: Ex. No. LXI Amine from Aldrich |

*Resolution of enantiomers is carried out by means of HPLC (Chiralpak AD, length 250 nm, diameter 4.6 mm, particle size 10 μ, eleunt: 95% n-heptane + 5% ethanol (the latter containing 1% water and 0.2% trifluoroacetic acid)).

EXAMPLE 69

2-(R,S)-2-[4-(2,4-Dimethyl-5,6,7, 8-tetrahydro-α-carbolin-9-yl)-methyl-phenyl]-2-cycloheptyl-acetic acid N2-hydroxybenz[]l)amide

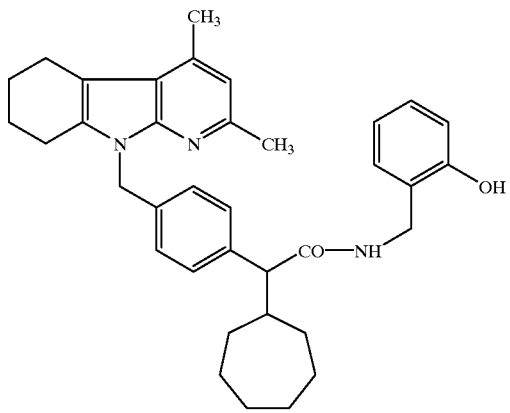

0.60 g of the compound from Example 58 are boiled under reflux for 22 hours with 33 mg of palladium (10% on animal carbon) and 33 mg of para-toluenesulphonic acid monohydrate in 3 ml of methanol and 0.6 ml of water under argon as a protective gas. If reaction is incomplete (TLC checking, diclhioromethane: ethanol =50:1). 33 mg of palladium (10% on animal carbon) and 33 mg of para-toluenesulphonic acid monohydrate are added once more and the mixture is boiled under reflux for a further 24 hours. The catalyst is filtered off hot with suction and washed with plenty of hot methanol, and the filtrate is evaporated. After drying in a high vacuum over phosphorus pentoxide, 0.52 g of product are obtained $R_f$=0.33 (dichloromethane: ethanol=50:1)

EXAMPLE 70

2-(R,S)-2-[4-(3-Hydroxymetyl-β-carbolin-9-yl)methyl-phenyl]-2-cyclo-pentyl-acetic acid N-(R)-phenylglycinolamide

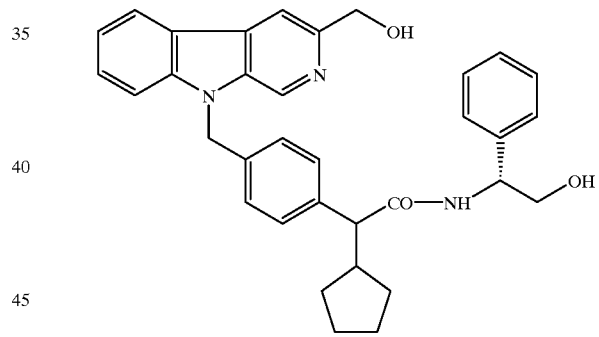

500 mg (0.868 mmol) of the compound from Example 31 are treated dropwise with 1.737 ml (1.737 mmol) of a 1 M lithium aluminium hydride solution in tetrahydrofuran under argon at 0° C. in 5 ml of anhydrous tethydrofiuran and stirred at about 20° C. for 4 h. The reaction mixture is treated cautiously with 5 ml of water and adjusted to a pH of about 2 using 2 M aqueous hydrochloric acid. The aqueous phase is extracted several times with diethyl ether and dichloromethane, dried with sodium sulphate and evaporated. The crude product is purified by chromatography on silica gel 60 (Merck, dichioromethane to dichloromethane: methanol 50:1).

Yield: 0.12 g $R_f$=0.26 (dichioromethane: ethanol=20:1)

The compounds of Table 4 are prepared in analogy to the procedure of Example 70:

TABLE 4

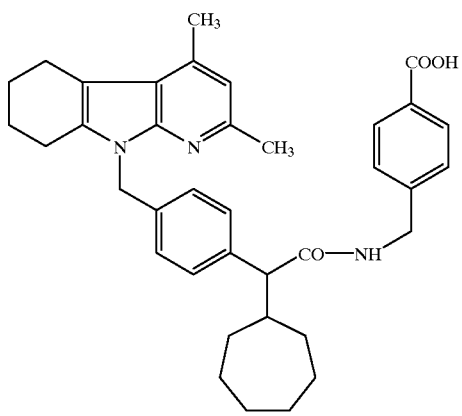

| Ex. No. | Y | 1 | R_f (solvent) | Starting material |
|---|---|---|---|---|
| 71 | 4-CH$_2$OH | rac | 0.47 (C) | Ex. No. 60 |
| 72 | 3-CH$_2$OH | rac | 0.26 (C) | Ex. No. 59 |

EXAMPLE 73

2-(R,S)-2-[4-(2,4-Dimethyl-5,6,7,8-tetrahydro-α-carbolin-9-yl)-methyl-phenyl]-2-cycloheptyl-acetic acid N-(4-carboxybenzyl)amide

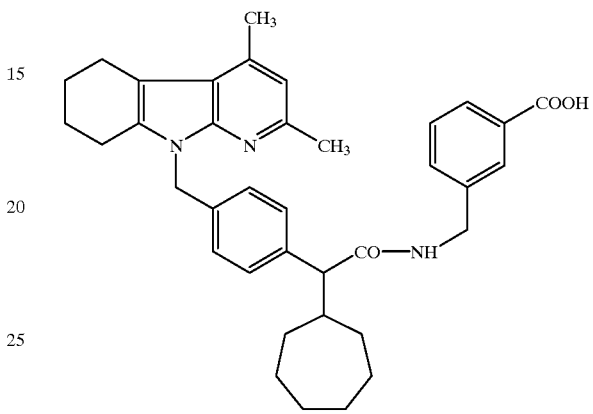

0.325 g (0.55 mmol) of the compound from Example 60 is reacted at 60° C. with 0.5 ml of aqueous 2 M sodium hydroxide solution in 3 ml of methanol for 18 h. If the reaction is still not complete according to thin-layer analysis (solvent F), a further 0.5 ml of aqueous 2 M sodium hydroxide solution in 1 mnl of methanol is added and the mixture is then boiled under reflux for 24 h. The reaction mixture is cooled and adjusted to a pH of about 4 using 1 M hydrochloric acid, and the precipitate which is deposited is filtered off with suction, washed with water and petroleum ether: diethyl ether=5:1 and freed from the residual solvents in a high vacuum over phosphorus pentoxide.

Yield: 0.154 g
R$_f$=0.50 (dichloromethane: methanol: acetic acid=90:10:2)

EXAMPLE 74

2-(R,S)-2-[4-(2,4-Dimethyl-5,6,7,8-tetrahydro-α-carbolin-9-yl)-methyl-phenyl]-2-cycloheptyl-acetic acid N-(3-carboxybenzyl)amide

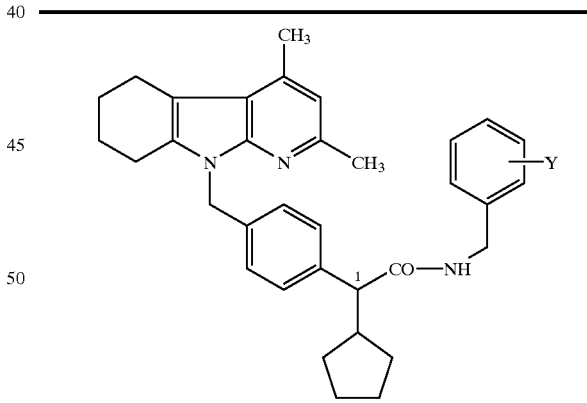

The title compound can be prepared from the compound of Example 59 analogously to the procedure of Example 73.

R$_f$=0.27 (dichloromethane: ethanol=20:1)

The compounds shown in Tables 5, 6, 7, 8, 9 and 10 are prepared in analogy to the procedure of Example 1:

TABLE 5

| Ex. No. | Y | 1 | M.p. | Starting material |
|---|---|---|---|---|
| 75 | 3-OH | rac | 177–178 | Carboxylic acid: Ex. No. LXII Amine: US 43 88 250 |
| 76 | 4-OH | rac | 183–184 | Carboxylic acid: Ex. No. LXII Amine: Ref.: C. Hartmann and J. P. Klinman, Biochemistry 30, 4605 (1991) |

TABLE 6

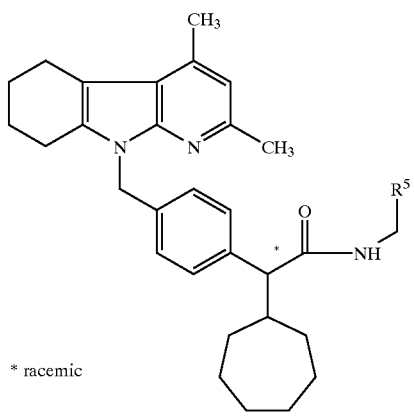

* racemic

| Ex. No. | R⁵ | $R_f$ (solvent) | Starting material |
|---|---|---|---|
| 77 | 2-pyridyl-CH₂ | 0.20 (C) | Carboxylic acid: Ex. No. LXV Amine from Aldrich |
| 78 | 3-pyridyl-CH₂ | 0.12 (C) | Carboxylic acid: Ex. No. LXV Amine from Aldrich |
| 79 | 4-pyridyl-CH₂ | 0.19 (C) | Carboxylic acid: Ex. No. LXV Amine from Aldrich |
| 80 | 2-thienyl-CH₂ | 0.24 (D) | Carboxylic acid: Ex. No. LXV Amine from Aldrich |

TABLE 7

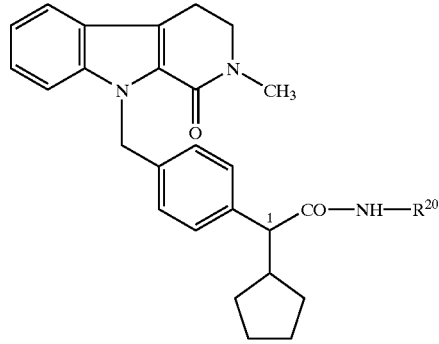

| Ex. No. | 1 | –R²⁰ | $R_f$ (solvent) | Starting material |
|---|---|---|---|---|
| 81 | rac | CH(C₆H₅)(CH₃)CH₂OH | 0.10 (P) | Acid: Ex. No. LXXIX Amine from Aldrich |
| 82 | rac | CH(C₆H₅)CH₂CH₃ | 0.28 (P) | Acid: Ex. No. LXXIX Amine from Aldrich |

TABLE 8

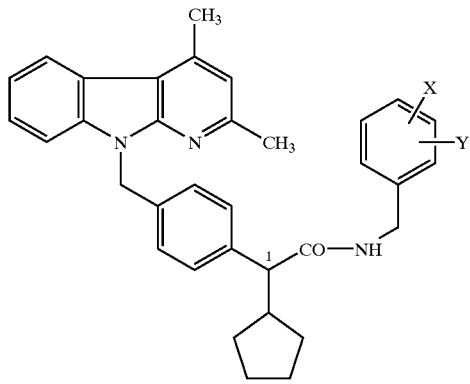

| Ex. No. | 1 | X | Y | M.p. (° C.) $R_f$ (solvent) | MS (FAB) | Starting material a) Reference b) Distributor c) Synthesis from Ex. No. |
|---|---|---|---|---|---|---|
| 83 | rac | 3-OCH₃ | 4-OCH₃ | 179 0.50 (A) | 562 (100%) 154 (80%) | Carboxylic acid: c) Ex. No. LXI Amine from Aldrich. |

TABLE 8-continued

| Ex. No. | 1 | X | Y | M.p. (° C.) R$_f$ (solvent) | MS (FAB) | Starting material a) Reference b) Distributor c) Synthesis from Ex. No. |
|---|---|---|---|---|---|---|
| 84 | rac | 3-CH$_3$ | 5-CH$_3$ | 212 0.60 (B) | 530 (100%) | Carboxylic acid: c) Ex. No. LXI Amine from Emka-Chemie. |
| 85 | rac | 3-Cl | 5-Cl | 212 0.18 (M) | 570 (100%) 196 (50%) | Carboxylic acid: c) Ex. No. LXI Amine from Maybridge. |
| 86 | rac | 3-OH | 4-OH | 137 0.39 (A) | 534 (100%) 307 (60%) | Carboxylic acid: c) Ex. No. LXI Amine from Aldrich. |
| 87 | rac | 3-OCH$_3$ | 4-OH | 135 0.65 (A) | 548 (80%) 154 (100%) | Carboxylic acid: c) Ex. No. LXI Amine from Aldrich. |

TABLE 9

| Ex. No. | 1 | D | M.p. (° C.) R$_f$ (solvent) | MS (FAB) | Starting material* a) Reference b) Distributor c) Synthesis from Ex.No |
|---|---|---|---|---|---|
| 88 | rac | iPr | 210 0.37/0.31 (A) | 506 (100%) 154 (60%) | Carboxylic acid: Ex. No. LXXXII |
| 89 | rac | iBu | — 0.30 (A) | 520 (100%) 154 (50%) | Carboxylic acid: Ex. No. LXXX |

*(R)-Phenylglycinol is commercially available from Aldrich.

TABLE 10

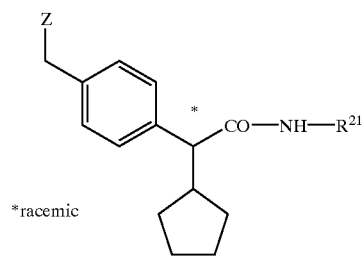

*racemic

| Ex. No. | -Z | -R²¹ | M.p. (° C.) $R_f$ (solvent) | Starting material from Ex. No. |
|---|---|---|---|---|
| 90 | (1-methyl-2,3,4,9-tetrahydro-1H-β-carbolin-1-yl, oxo) | C₆H₅, ethyl | 188–189 | LXXXIX |
| 91 | (1-methyl-2,3,4,9-tetrahydro-1H-β-carbolin-1-yl, oxo) | C₆H₅, CH(CH₃)CH₂OH | 0.024 (P) | LXXXIX |
| 92 | (5,7-dimethyl-1-methyl-2,3,4,9-tetrahydro-1H-β-carbolin-1-yl, oxo) | C₆H₅, CH(CH₃)CH₂OH | 207–208 | XC |
| 93 | (5,7-dimethyl-1-methyl-2,3,4,9-tetrahydro-1H-β-carbolin-1-yl, oxo) | C₆H₅, ethyl | 211–212 | XC |

The compounds of Table II are prepared analogously to the procedure of Example Nos. 1, 2 and 3:

TABLE 11

| Ex. No. | Z | D | 1 | M.p. (° C.) R$_f$ (solvent) | MS (FAB) | Starting material from Ex. No. |
|---|---|---|---|---|---|---|
| 94 | 5,6,7,8-tetrahydro-9-methyl-2-methyl-pyrido[2,3-b]indole | cHept | S | 0.23 (B) | | 27 |
| 95 | 5,6,7,8-tetrahydro-9-methyl-2-methyl-pyrido[2,3-b]indole | cHept | R | 0.17 (B) | | 27 |
| 96 | 4-CF$_3$-5,6,7,8-tetrahydro-9-methyl-2-methyl-pyrido[2,3-b]indole | cPent | S | 0.29 (A) | | 20 |
| 97 | 4-CF$_3$-5,6,7,8-tetrahydro-9-methyl-2-methyl-pyrido[2,3-b]indole | cPent | R | 0.29 (A) | | 20 |
| 98 | 4-Me-9-methyl-2-methyl-pyrido[2,3-b]indole | cHex | S | 0.23 (D) | | 38 |
| 99 | 4-Me-9-methyl-2-methyl-pyrido[2,3-b]indole | cHex | R | 0.21 (D) | | 38 |
| 100 | 4-Me-9-methyl-2-methyl-pyrido[2,3-b]indole | iPr | S | 208° C. | 506 (100%) 154 (40%) | 88 |

TABLE 11-continued

| Ex. No. | Z | D | 1 | M.p. (° C.) R$_f$ (solvent) | MS (FAB) | Starting material from Ex. No. |
|---|---|---|---|---|---|---|
| 101 | 4-Me, 2-Me α-carboline (N-Me) | iPr | R | 204° C. | 506 (100%) 154 (40%) | 88 |
| 102 | 4-Me, 2-Me α-carboline (N-Me) | iBu | S | 182° C. | | 89 |
| 103 | 4-Me, 2-Me α-carboline (N-Me) | iBu | R | 206° C. | | 89 |
| 104 | tetrahydro α-carboline (N-Me) | cPent | rac | 0.34 (C) | | CV |
| 105 | 4-CF$_3$, 2-Me α-carboline (N-Me) | cPent | rac | 0.44 (E) 0.56 | | CVI |
| 106 | 4-CF$_3$, 2-Me α-carboline (N-Me) | cPent | S | 0.56 (E) | 586 (100%) 154 (94%) | CVI |

TABLE 11-continued

[Structure: 4-(ZCH2)-phenyl-CH(D)-CONH-CH(Ph)-CH2OH, with (S) configuration at the phenyl-bearing carbon]

| Ex. No. | Z | D | 1 | M.p. (° C.) $R_f$ (solvent) | MS (FAB) | Starting material from Ex. No. |
|---|---|---|---|---|---|---|
| 107 | 4-CF₃-2-Me-9-Me-9H-pyrido[2,3-b]indol-3-yl | cPent | R | 0.44 (E) | | CVI |
| 108 | 2-Me-9-Me-9H-pyrido[2,3-b]indol-3-yl | cPent | rac | 0.26 (E) 0.31 | | CVII |
| 109 | 2-Me-9-Me-9H-pyrido[2,3-b]indol-3-yl | cPent | S | 0.55 (C) | | CVII |
| 110 | 2-Me-9-Me-9H-pyrido[2,3-b]indol-3-yl | cPent | R | 0.57 (C) | | CVII |
| 111 | 3-CF-5,6,7,8-tetrahydro-9H-pyrido[2,3-b]indol-2-yl | cPent | rac | 0.45 (C) | | CVIII |
| 112 | 3-CF-5,6,7,8-tetrahydro-9H-pyrido[2,3-b]indol-2-yl | cPent | rac | 0.4 C | | CIX |
| 113 | 4-Me-9H-pyrido[2,3-b]indol-3-yl | cPent | rac | 0.37 C | | CX |

TABLE 11-continued

| Ex. No. | Z | D | 1 | M.p. (° C.) R_f (solvent) | MS (FAB) | Starting material from Ex. No. |
|---|---|---|---|---|---|---|
| 114 | 1-Me, 4-Me β-carboline (pyridine N) | cPent | S | 0.37 (C) | | CX |
| 115 | 1-Me, 4-Me β-carboline (pyridine N) | cPent | R | 0.37 (C) | | CX |
| 116 | 1-Me-2-Me-1-oxo-tetrahydro-β-carboline | cPent | diaA | 194° C. | | 81 |
| 117 | 1-Me-2-Me-1-oxo-tetrahydro-β-carboline | cPent | diaB | 137° C. | | 81 |

The compounds of Table 12 are prepared analogously to the procedure of Example Nos. 1, 2 and 3:

TABLE 12
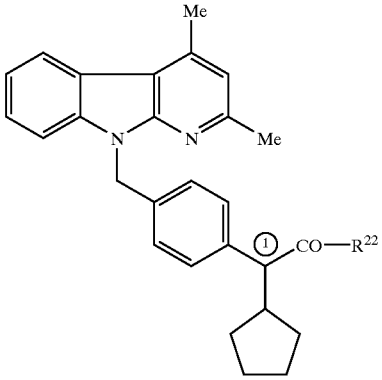
| Ex. No. | 1 | $R_{22}$ | M.p. (° C.) $R_f$ (solvent) | MS (FAB) | Starting material from Ex. No. |
|---|---|---|---|---|---|
| 118 | rac | —NH—CH(Ph)—CO₂Et | 0.82 (C) | 574 (100%) | LXI |
| 119 | rac | —NH—CH(3-HO-C₆H₄)—CO₂Me | 0.57 (C) 0.62 | 576 (100%) | LXI |
| 120 | rac | —NH—CH(4-HO-C₆H₄)—CO₂Me | 0.43 (C) 0.48 | | LXI |
| 121 | rac | —NH—CH(2-HO-C₆H₄)—CO₂Me | 0.52 (C) | | LXI |
| 122 | rac | —NH—CH(3,4-(HO)₂-C₆H₃)—CO₂Me | 0.47 (C) | | LXI |

TABLE 12-continued
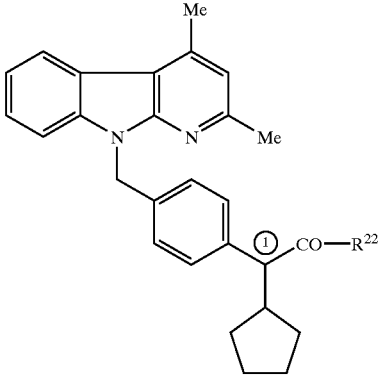
| Ex. No. | 1 | $R_{22}$ | M.p. (° C.) $R_f$ (solvent) | MS (FAB) | Starting material from Ex. No. |
|---|---|---|---|---|---|
| 123 | rac | 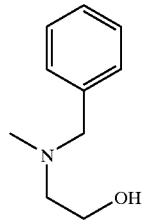 | 0.17 (D)<br>0.32 | | LXI |
| 124 | rac | 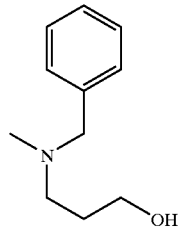 | 0.43 (C) | | LXI |
| 125 | rac | 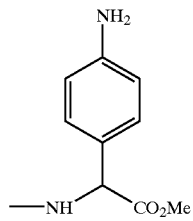 | 0.57 (C) | | LXI |
| 126 | rac | 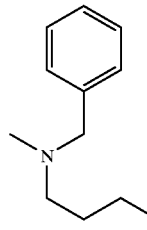 | 0.41 (C) | | LXI |

TABLE 12-continued
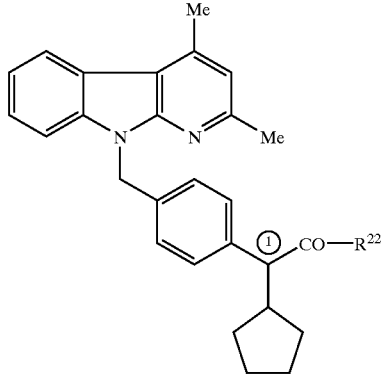
| Ex. No. | 1 | $R_{22}$ | M.p. (° C.) $R_f$ (solvent) | MS (FAB) | Starting material from Ex. No. |
|---|---|---|---|---|---|
| 127 | rac | 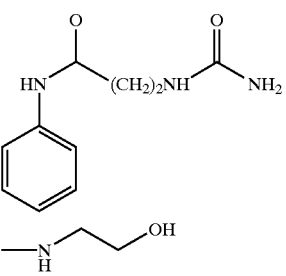 | 0.14 (C) | | 137 |
| 128 | S | 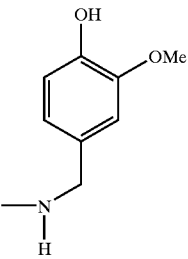 | 187° C. | 548 (100%) 154 (80%) 137 (85%) | LXI |
The compounds of Table 13 are prepard analogously to the procedure of Example No. 73:
TABLE 13
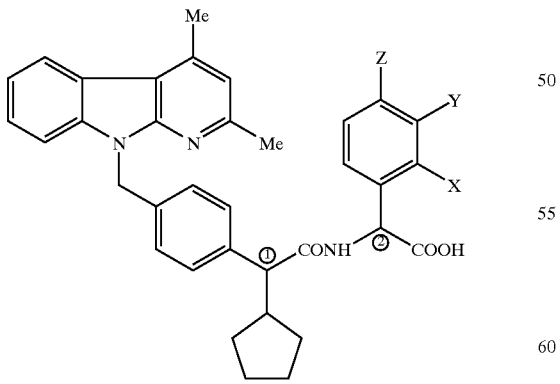
| Example No. | ①/② | X | Y | Z | M.p. [° C.] $R_f$ (solvent) | Starting material from Ex. No. |
|---|---|---|---|---|---|---|
| 129 | rac/rac | H | H | H | 0.15 (S) | 118 |
| 130 | rac/rac | H | OH | H | 0.18 (T) | 119 |

TABLE 13-continued

[Structure diagram]

| Example No. | ①/② | X | Y | Z | M.p. [° C.] $R_f$ (solvent) | Starting material from Ex. No. |
|---|---|---|---|---|---|---|
| 131 | rac/rac | H | H | OH | 0.24 0.68 (S) 0.76 | 120 |
| 132 | rac/rac | OH | H | H | 0.16 (T) 0.24 | 121 |

The compounds of Table 14 are prepared analogously to the procedure of Example No. 70:

TABLE 14

[Structure diagram]

| Example No. | 1̂/2̂ | X | Y | Z | M.p. [° C.] $R_f$ (solvent) | Starting material from Ex. No. |
|---|---|---|---|---|---|---|
| 133 | rac/rac | H | OH | H | 0.30 (A) | 119 |
| 134 | rac/rac | H | H | OH | 0.25 (A) | 120 |
| 135 | rac/rac | OH | H | H | 0.33 (A) | 121 |
| 136 | rac/rac | H | OH | OH | 0.23 (A) | 122 |
| 137 | rac/rac | H | H | $NH_2$ | 0.31 (C) | 125 |

EXAMPLE NO. 138

2-(R,S)-2-[4(2,4-Dimethyl-α-carbolin-9-yl)methyl-phenyl]-2-cyclopentyl-acetic acid N-[1-(R,S)-1-(4-acetamido-phenyl)-2-hydroxy-ethyl]amide

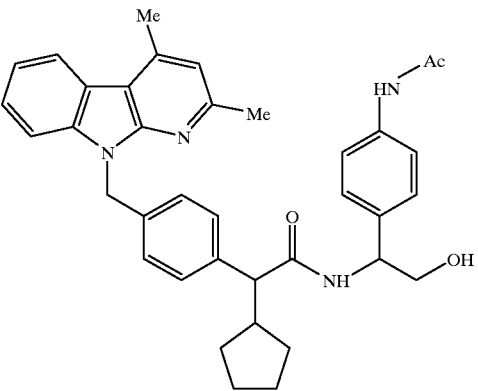

Part A 0.60 g (1.10 mmol) of the compound from Example No. 137 is treated with 192 μl (3.29 mmol) of triethylamine in 10 ml of dichloromethane and then reacted at 0° C with 70 μl (0.99 mmol) of acetyl chloride. After a stirring time of 3 hours, in which the reaction temperature rises to 20° C., the mixture is shaken successively with 1 M hydrochloric acid, 0.1 M aqueous sodium hydroxide solution and water, and the organic phase is dried with magnesium sulphate and evaporated

Part B

The crude product thus obtained shows a double acetylation (631, 57%, M$^+$+H/653, 6%, M$^+$+Na) in the mass spectrum (FAB). It is therefore reacted with 2 M sodium hydroxide solution at 20° C. for one hour in 6 ml of methanol. The pH is then adjusted to 2 using 1 M hydrochloric acid and the mixture obtained is extracted with ethyl acetate. The organic phase is washed with water until neutral, dried with magnesium sulphate and evaporated in vacuo. Drying in a high vacuum yields 0.28 g of product. $R_f$=0.17 (Dichloromethane: ethanol=20:1)

EXAMPLE NO. 139

2-(R,S)-2-[4(2,4-Dimethyl-α-carbolin-9-yl)-methyl-phenyl]-2-cyclopentyl-acetic acid N-[1 -(R,S)-1(4-acetamido phenyl)-2-acetoxy-ethyl]amide

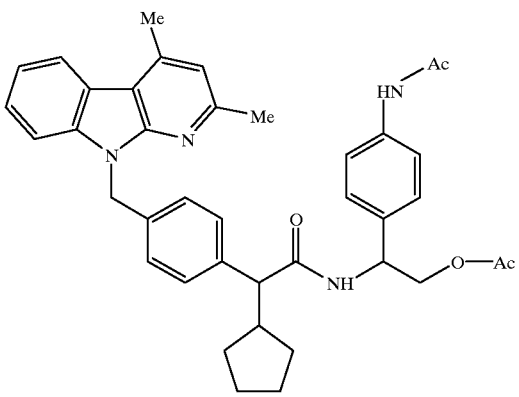

If the compound from Example No. 137 is reacted with 4 equivalents each of triethylamine and acetyl chloride analogously to Part A of the procedure from Example No. 139, the title compound is obtained.

$R_f$=0.56 Dichloromethane: ethanol=20:1)

The compounds of Table 15 are prepared analogously to the procedure of Example No. 138:

TABLE 15

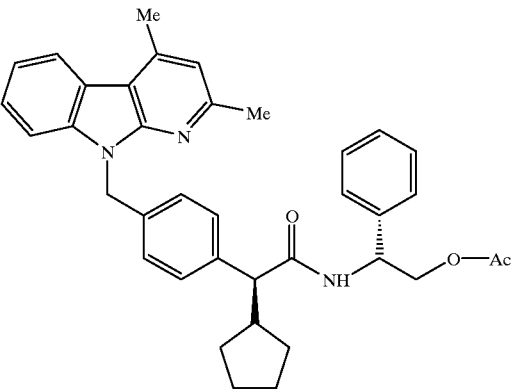

| Example No. | 1/2 | $R^{23}$ | M.p. [° C.] $R_f$ (solvent) | Starting material from Ex. No. |
|---|---|---|---|---|
| 140 | rac/rac | nBu | 0.49 (A) | 137 |
| 141 | rac/rac | Et | 0.81 (U) | 137 |

EXAMPLE NO. 142

2(S)2-[4-(2,4-Dimethyl-α-carbolin-9-yl)methyl-phenyl]-2-cyclopentyl-acetic acid N-[1-(R)-1-phenyl-2-acetoxy-ethyl]amide

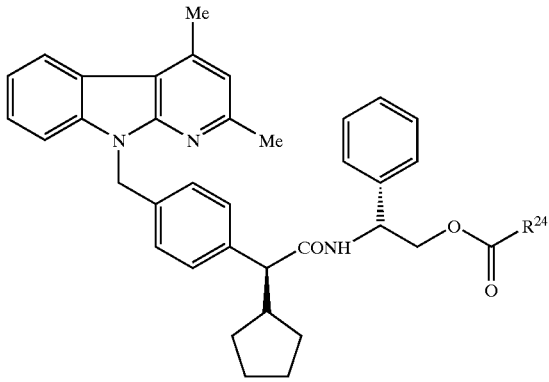

4.5 g (8.46 mmol) of the compound No. 2 are suspended in 300 ml of dichloromethane, treated with 2.05 ml (25.4 mmol) of pyridine and 1.82 ml (25.4 mmol) of acetyl), chloride in 30 ml of dichloromethae and reacted at 20° C. for 20 hours. The mixture extrated with buffer (Merck) of pH=2 and water, dried with sodium sulphate and evaporated. After precipitating by stirring with methanol and subsequently drying in a high vacuum over phosphorus pentoxide, 3.6 g of product are obtained.

$R_f$=0.62 (Petroleun ether: ethyl acetate=1:1)

The compounds of Table 16 are prepared analogously to the procedure of Example No. 142:

TABLE 16

| Example No. | $R^{24}$ | M.p. [° C.] $R_f$ (solvent) | Starting material from Ex. No. |
|---|---|---|---|
| 143 | —Et | 0.25 (D) | 2 |
| 144 | —CH$_2$OAc | 0.29 (D) | 2 |
| 145 | —CH$_2$OCH$_2$Ph | 0.27 (D) | 2 |
| 146 | cis-(CH$_2$)$_7$—Z—CH=CH—(CH$_2$)$_7$CH$_3$ | 0.52 (D) | 2 |
| 147 | —(CH$_2$)$_{14}$—CH$_3$ | 0.69 (G) | 2 |
| 148 | —Ph | 0.65 (C) | 2 |

TABLE 16-continued

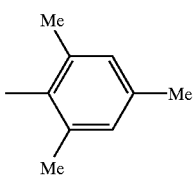

| Example No. | R²⁴ | M.p. [° C.] R_f (solvent) | Starting material from Ex. No. |
|---|---|---|---|
| 149 | (2,6-dimethyl-4-methylphenyl) Me-Ar(Me,Me)-Me | | 2 |
| 150 | -tBu | 0.38 (C) | 2 |

EXAMPLE NO. 151

2-(S)-2-[4-(2,4-Dimethyl-α-carbolin-9-yl)methyl-phenyl]-2-cyclopentyl-thioaceticacid N-[1-(R)-1-phenyl-2-acetoxy-ethyl]amide

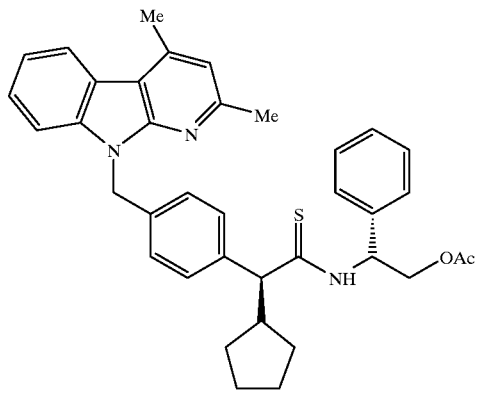

1.5 g (2.6 mmol) of the compound from Example No. 142 are treated with 1.27 g (3.13 mmol) of 2,4bis-(4-methoxyphenyl)-1,3dithia-2,4-diphosphetane-2,4-di-sulphide (Lawesson's reagent) in 50 ml of dioxane and boiled under reflux for 5 hours. The reaction mixture is evaporated to dryness in vacuo and purified by chromatography on silica gel MATREX™ silica Si (Amicon, Grace Company/20 μ/MPLC column/ dichloromethane: ethanol= 100:1); yield: 665 mg.

$R_f$=0.53 (Petroleum ether: ethyl acetate=2:1)

MS (FAB): m/e=612 (4%, [M+Na]⁺), 590 (100%, [M+H]⁺), 529 (19%, M⁺-AcOH).

EXAMPLE 152

2-(S)-2-[4-(2,4-Dimethyl-α-carbolin-9-yl)methyl-phenyl]-2-cyclopentyl-acetic acid N-[1-(R)1-phenyl-2-[2-hydroxy-acet)-oxy ]-ethyl]amide

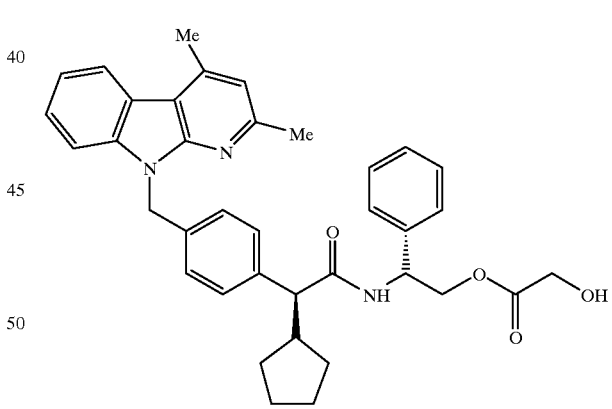

1.45 g (2.13 mmol) of the cornpound from Example No. 145 are hydrogenated with hydrogen on palladium (5% on animal carbon) at 20° C. and normal pressure in 100 ml of THF. After 18 hours, the mixture is filtered off with suction through kieselguhr, washed several times wvith methanol and dichloromethane, and the combined organic solutions are evaporated. The solid residue is stirred with pentane, filtered off with suction and freed from the residual solvent in a high vacuum.

$R_f$=0.31 (Petroleum ether: ethyl acetate=1:1)

EXAMPLE NO. 153

2(S)-2-[4-(2,4-Dimethyl-α-carbolin-9-yl)methyl-phenyl]-2-cyclopentyl-thoaceticacid N-[1(R)-1-phenyl-2-hydroxyethyl]-amide

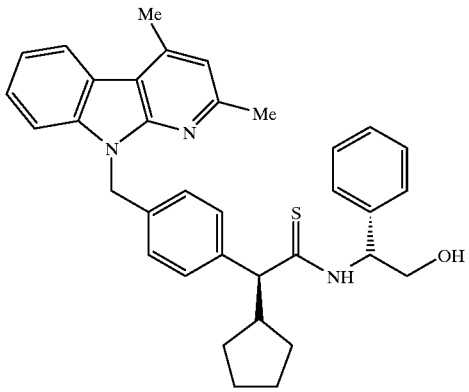

The title compound is prepared at 20° C. from the compound of Example No. 151 in DME as a solvent analogously to the synthesis procedure from Example No. 73.

$R_f$=0.24 (Dichloromethane: ethanol=50:1)

EXAMPLE NO. 154

2-[4-(2,4-Dimethyl-α-carbolin-9-yl)-methyl-phenyl]-2-cyclopentyl-acetic acid N-[1-(thien-2-yl)-1-methoxycarbonyl-methyl]-amide

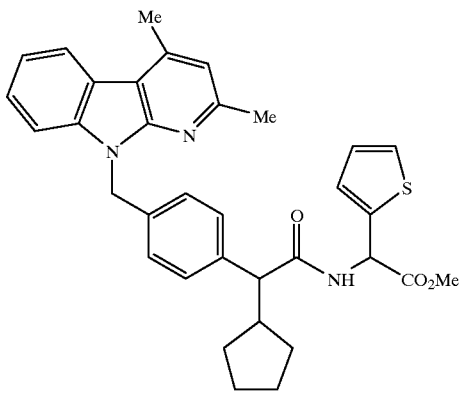

The title compound is prepared from the compound of Example No. LXII and (R,S)——(thien-2-yl)—glycine methyl ester analogously to the synthesis procedure of Example Nos. 1, 2 and 3.

$R_f$=0.67 (Dichloromethane: ethanol=20:1)

EXAMPLE NO. 155

2-[4-(2,4-Dimethyl-α-carbolin-9-yl)-methyl-phenyl]-2-cyclopentyl-acetic acid N-[1-thien-2-yl)-2-hydroxy-ethyl]-amide

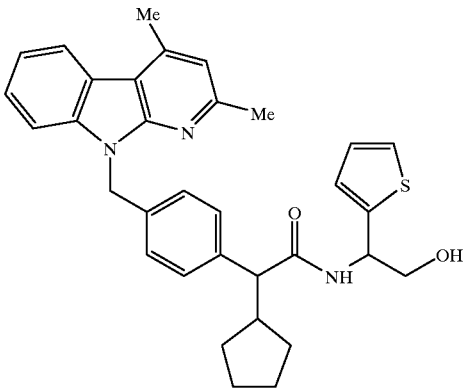

The title compound is prepared from the compound of Example No. 154 analogously to the synthesis procedure of Example No. 70.

$R_f$=0.21 (Dichloromethane: ethanol=50:1)

EXAMPLE NO. 156

2-(S)-2-[4-(2,4-Dimethyl-α-carbolin-9-yl)methyl-phenyl]-2-cyclopentyl-acetic acid N-[1-(R)-1-phenyl-2-(2,4,6-trimethyl-benzoyl-oxy)ethyl]-amide

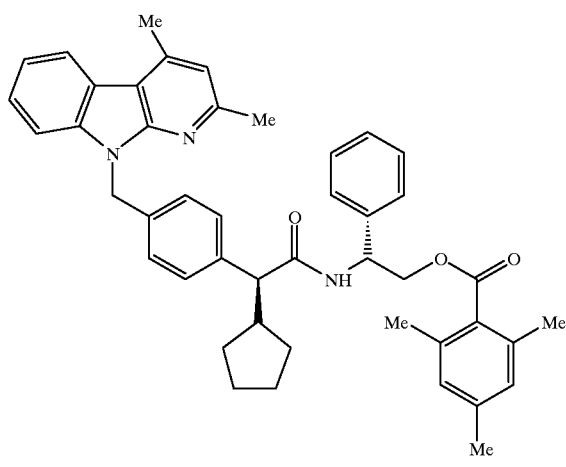

The compound is prepared from Example No. 2 is reacted to give the title compound analogously to the procedure of Example No. 142.

$R_f$=0.26 (Mobile phase D)

EXAMPLE 157

1-(R,S)-1-Phenyl-2-triphenylmethyloxy-ethyl 2-(R,S)-2-[4-(2,4-dimethyl-α-carbolin-9-yl)methyl-phenyl]-2-cyclopentyl-acetate

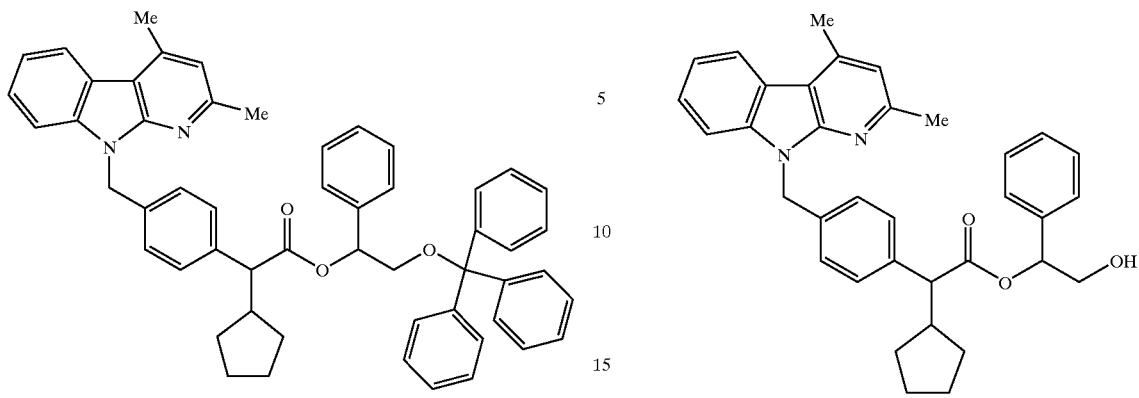

1.0 g (2.42 mmol) of the compound from Example LXI is reacted with 1 ml (7.27 mmol of triethylamine and 206 μl (2.67 mmol) of mesyl chloride in 30 ml of DMF at −30° C. for 2 h, then treated dropwise with a solution of 1.1 g (2.9 mmol) of the compound from Example No. CXI and 296 mg (2.42 mmol) of DMAP in 10 ml of DMF and stirred for about 20 h while graually warming to 20° C. For working up, the mixture is stirred into ether/water, the phases are separated, and the organic phase is extracted with aqueous 1 M sodium hydroxide solution and washed with water. The organic phase is dried with magnesium sulphate and evaporated - finally in a high vacuum; yield: 1.0 g.
$R_f$=0.44 (Petroleum ether: ethyl acetate=5:1)

EXAMPLES 158 and 159

1-(R,S)-1-Phenyl)-2-triphenylmethyloxy-ethyl [2-(R,S)-2-[4-(2,4-dimethyl-α-carbolin-9-yl)methyl-phenyl]-2-cyclopentyl-acetate 1.0 g (1.29 mmol) of the compound from Example No. 157 is stirred with 5 ml of trifluoroacetic acid in 10 ml of THF and 5 ml of water at 20° C. for 48 h. The mixture is then stirred with 300 ml of ether and 200 ml of aqueous sodium hydrogen carbonate solution, the phases are separated after evolution of carbon dioxide has subsided and the organic phase is extracted with buffer of pH=7 (Merck) and dried with magnesium sulphate. After evaporating the solvents, a crude product is obtained which is purified by chromatogphy on silica gel (Merck/petroleum ether: ethyl acetate=5:1) and separated into the diastereomers.
Racemic diastereomer A)
Yield: 300 mg
$R_f$=0.54 (Petroleum ether: ethyl acetate=2:1)
Racemic diastereomer B)
Yield: 320 mg
$R_f$=0.42 (Petroleum ether: ethyl acetate 2:1)
The compounds of Table 17 are prepared analogously to the procedure of Exaimp[]eNos. 1, 2 and 3:

TABLE 17

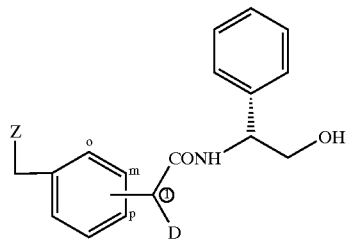

| Ex. No. | Z | Position (o, m or p) | î | D | $R_f$ (solvent) | MS | Starting material Ex. No. |
|---|---|---|---|---|---|---|---|
| 160 | 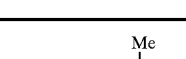 Me | p | — | H | 0.30 (C) | FAB: 464 (100%) | CXLI |
| 161 | 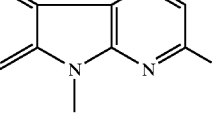 | p | rac | cPent | 0.35 (C) | FAB: 504 (95%) | CXLII |

TABLE 17-continued
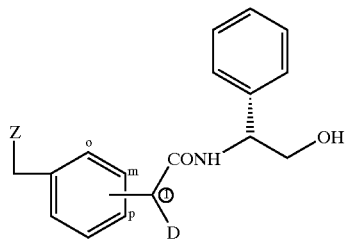
| Ex. No. | Z | Position (o, m or p) | î | D | $R_f$ (solvent) | MS | Starting material Ex. No. |
|---|---|---|---|---|---|---|---|
| 162 | | p | S | cPent | 0.35 (C) | | CXLII |
| 163 | | p | R | cPent | 0.35 (C) | | CXLII |
| 164 | | p | rac | cPent | 0.23/(C) 0.25 | FAB: 518 (51%) | CXLIII |
| 165 | | p | R | cPent | 0.29 (C) | | CXLIII |
| 166 | | p | S | cPent | 0.25 (C) | | CXLIII |
| 167 | | m | rac | cPent | 0.40 (C) | FAB: 532 (100%) | CXLIV |
| 168 | | p | rac | cPent | 0.26/0.22 (D) | FAB: 518 (100%) | CVL |
| 169 | | p | | | cPent | 0.26 (D) | CVL |

TABLE 17-continued

| Ex. No. | Z | Position (o, m or p) | î | D | R$_f$ (solvent) | MS | Starting material Ex. No. |
|---|---|---|---|---|---|---|---|
| 170 | [5H-pyrido[3,2-b]indole, N-Me, 3-Me] | p | | cPent | 0.22 (D) | | CVL |
| 171 | [6,7-diMe-α-carboline, N-Me] | p | rac | cPent | 0.37 (C) | | CVLI |
| 172 | [3-Me-α-carboline, N-Me] | p | rac | cPent | | | CVLII |
| 173 | [5,7-diMe-γ-carboline, N-Me] | p | rac | cPent | 0.19 (C) | FAB: 532 (100%) | CVLIII |
| 174 | [1,3-diMe-γ-carboline, N-Me] | p | rac | cPent | | | CIL |
| 175 | [1,3-diMe-γ-carboline, N-Me] | p | | cPent | | | CIL |
| 176 | [1,3-diMe-γ-carboline, N-Me] | p | | cPent | | | CIL |

TABLE 17-continued

[Structure: Z-CH2-phenyl(o,m,p positions)-C(D)(⊕)-CONH-CH(phenyl)-CH2-OH]

| Ex. No. | Z | Position (o, m or p) | î | D | R_f (solvent) | MS | Starting material Ex. No. |
|---|---|---|---|---|---|---|---|
| 177 | 4-Me, 2-Me, N-Me pyrido[2,3-b]indole | p | rac | Et | | | CI |
| 178 | 4-Me, 2-Me, N-Me pyrido[2,3-b]indole | p | rac | Me | | | CLI |
| 179 | 4-Me, 2-Me, N-Me pyrido[2,3-b]indole | p | rac | nPent | | | CLII |
| 180 | 4-Me, 2-Me, N-Me pyrido[2,3-b]indole | p | diaA | nPent | | | CLII |
| 181 | 4-Me, 2-Me, N-Me pyrido[2,3-b]indole | p | diaB | nPent | | | CLII |
| 182 | 4-Me, 2-Me, N-Me pyrido[2,3-b]indole | p | rac | CH2CH(Me)CH2Me (isobutyl-like) | | | CLIII |

TABLE 17-continued

| Ex. No. | Z | Position (o, m or p) | î | D | $R_f$ (solvent) | MS | Starting material Ex. No. |
|---|---|---|---|---|---|---|---|
| 183 | (2,4-dimethyl-α-carboline-9-yl, N-Me) | p | diA | isobutyl (Me-CH-Me with CH2 arms) | | | CLIII |
| 184 | (2,4-dimethyl-α-carboline-9-yl, N-Me) | p | diaB | isobutyl (Me-CH-Me with CH2 arms) | | | CLIII |

EXAMPLE 185

2-(R,S)-2-[4-(2,4-Dimethyl-α-carbolin-9-yl-methyl-phenyl]-2-cyclopentyl-acetic acid [N-benzyl, N-benzoyl]-amide

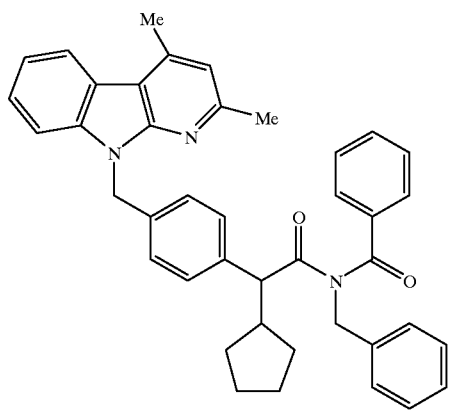

2.0 g (4.8 mmol) of the compound from Example No. LXI are reacted with 0.74 ml (5.3 mmol) of triethylamine and 0.41 ml (5.3 mmol) of mesyl chloride at −30° C. in anhydrous DMF for 1 h. A solution of 1.07 g (5.1 mmol) of N-benzamide-benznide and 1.42 ml (10.2 mmol) of triethylamine in 10 ml of anhydrous DMF is then added dropnise at −30° C. and stirred for 16 h while gradually warming to 20° C. The reaction mixture is stirred with ether and water, the phases are separated and the aqueous phase is washed after setting a pH of 4 and 7 in each case. The combined organic solutions are evaporated and purified by chromlatography on silica gel 60 (Merck / first dichloromethane: ethanol =60:1; then petroleum ether: ethyl acetate=4:1).

$R_f$=0.58 (Petroleum ether: ethyl acetate=2:1)

EXAMPLE 186

2-(R,S)-2-[4-(2,4-Dimethyl-α-carbolin-9-yl)methyl-phenyl]-2-cyclopentyl-acetic acid [N-benzoyl]-amide

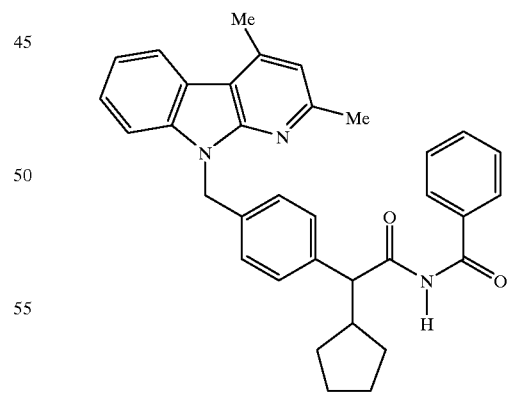

2.0 g (3.3 mmol) of the compound from Example No. 185 are reacted at 20° C. under a hydrogen pressure of about 1 bar on 2 g of palladium on animal carbon (5%) in dioxane for about 40 h. The mixture is then filtered off with suction through a Seitz filter and washed with dioxane, and the filtrate is evaporated. The crude product is precipitated by stirring with methanol at 60° C. and is filtered off with suction at 20° C., washed with cold methanol and dried over phosphorus pentoxide in vacuo.

$R_f$=0.49 (Petroleum ether: ethyl acetate=2:1)

EXAMPLE 187

2-(R,S)-2-[4-(2,4Dimethyl-α-carbolin-9-yl)-methyl-phenyl]-2-cyclopentyl-acetic acid [N-(1-(R,S)-1-phenyl-1-ethoxycarbonyl-methyl]-amide

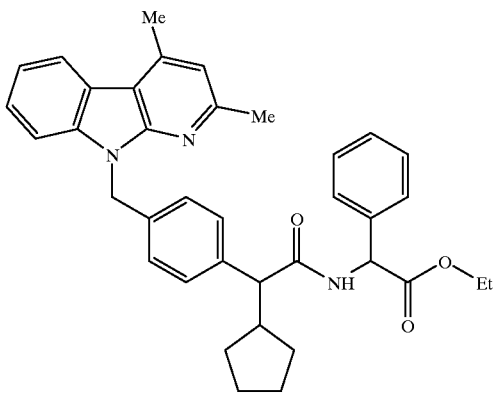

The compound from Example No. LXI is reacted to give the title compound analogously to the proceure of Example Nos. 1, 2 and 3.

EXAMPLE 188

2(R,S)-2-[4-(2,4-Dimethyl-α-carbolin-9-yl)-methyl-phenyl]-2-cyclopentyl-acetic acid [N-(1-(R,S)-1-phenyl-1-carboxy-methyl]-amide

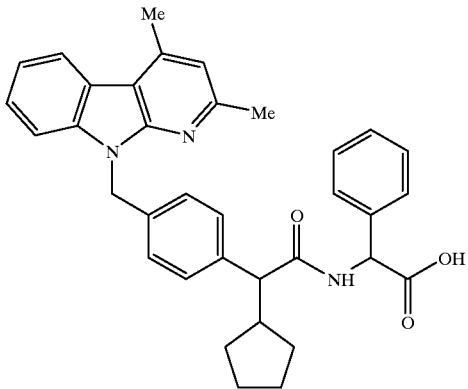

The compound from Example No. 187 is reacted to give the title compoud analogously to the proceure of Example No. 73.

EXAMPLE 189

1-1-(R,S)-2-hydroxy-phenyl-ethyl2-(R,S)-2-[4-(2,4-Dimethyl-α-carbolin-9-yl)methyl-phenyl]-2-cyclopentyl-acetate

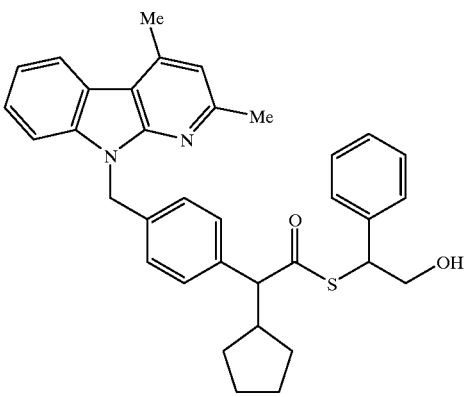

1 g (2.42 mmol) of the compound from Example No. LXI is reacted with, 1 ml (7.27 mmol) of triethylamine and 206 µl (2.67 mmol) of mesyl chloride for 1 h in 30 ml of DMF at −30° C. A solution of 1-(R,S)-1-phenyl-2-hydroxy-thioethanol in 10 ml of DMF is then added dropwise at the temperature mentioned and the mixture is stirred for a further hour. For working up, the reaction mixture is stirred into ether and aqueous sodium hydrogen carbonate solution. The organic phase is washed with buffer pH=2 and then pH=7, dried with magnesium sulphate and evaporated. The crude product is purified on silica gel 60 (Merck/petroleum ether: ethyl acetate=5:1); yield: 660 mg $R_f$=0.58 (Petroleum ether: ethyl acetate=2:1)

What is claimed is:

1. A method of treating obesity in a patient in need thereof comprising administering to such patient an amount effective thereof of a compound of the formula

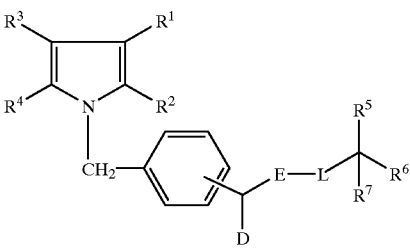

in which $R^1$ and $R^2$ form a pyridyl ring which is optionally substituted 1 to 3 times by identical or different substituents;

$R^3$ and $R^4$, including the double bond connecting them, form a phenyl ring or a 6-membered cycloalkene ring each of which are optionally substituted 1 to 3 times by identical or different substituents;

wherein said substituents on the pyridyl, phenyl or cycloalkene ring are selected from the group consisting of halogen, trifluoromethyl, carboxyl, hydroxyl, straight-chain or branched $C_1$–$C_6$ alkoxy, straight-chain or branched $C_1$–$C_6$ alkoxycarbonyl, or an optionally substituted straight-chain or branched $C_1$–$C_6$ alkyl wherein the substituents on the alkyl group are hydroxyl or straight-chain or branched alkoxy having up to 4 carbon atoms, D represents hydrogen, cycloalkyl having 4 to 12 carbon atoms or straight-chain or branched alkyl having up to 12 carbon atoms, E represents the —CO— or —CS— group, L represents a group of the formula —NR$^9$
wherein
R$^9$ denotes hydrogen or straight-chain or branched alkyl having up to 6 carbon atoms, which is optionally substituted by hydroxyl or phenyl,
R$^5$ represents phenyl which is optionally substituted 1 to 3 times by identical of different substituents selected from the group consisting of nitro, carboxyl, halogen, cyano straight-chain or branched C$_2$–C$_6$ alkenyl, straight-chain or branched C$_1$–C$_6$ alkoxycarbonyl or optionally substituted C$_1$–C$_6$ straight-chain or branched alkyl wherein the substituents on the alkyl are hydroxyl, carboxyl, straight-chain or branched C$_1$–C$_6$ alkoxy, or straight-chain or branched C$_1$–C$_6$ alkoxycarbonyl,
or said phenyl ring is further optionally substituted by a group of the formula —OR$^{10}$ or —NR$_{11}$R$_{12}$,
wherein
R$^{10}$ denotes hydrogen or straight-chain or branched alkyl or alkenyl each having up to 6 carbon atoms,
R$^{11}$ and R$^{12}$ are identical or different and denote phenyl, hydrogen or straight-chain or branched alkyl having up to 6 carbon atoms or straight-chain or branched acyl having up to 8 carbon atoms, which is optionally substituted by a group of the formula —NR$^{13}$N$^{14}$,
wherein
R$^{13}$ and R$^{14}$ are identically or different and denote hydrogen or straight-chain or branched acyl having up to 8 carbon atoms,
R$^6$ represents hydrogen, carboxyl or straight-chain or branched alkoxycarbonyl having up to 5 carbon atoms, or represents straight-chain or branched alkyl having up to 6 carbon atoms, which is optionally substituted by hydroxyl or by a group of the formula —O—CO—R$^{15}$,
wherein
R$^{15}$ denotes phenyl which is optionally substituted up to 3 times by identical or different halogen or hydroxyl substituents or by straight-chain or branched alkyl having up to 5 carbon atoms, or straight-chain or branched alkyl or alkenyl each having up to 22 carbon atoms, each of which is optionally substituted by a group of the formula —OR$^{16}$,
wherein
R$^{16}$ is hydrogen, benzyl, triphenylmethyl or straight-chain or branched acyl having up to 6 carbon atoms,
R$^7$ represents hydrogen, or
R$^6$ and R$^7$ together represent the group of the formula =O,
or an isomeric form of said compound or a salt thereof.

2. The method of claim 1, wherein
R$^1$ and R$^2$ form a pyridyl ring which is optionally substituted 1 to 2 times by identical or different substituents;
R$^3$ and R$^4$, including the double bond connecting them, form a phenyl ring or a 6-membered cycloalkene ring each of which are optionally substituted 1 to 2 times by identical or different substituents,
wherein said substituents on the pyridyl, phenyl or cycloalkene ring are selected from the group consisting of fluorine, chlorine, bromine, trifluoromethyl, carboxyl, hydroxyl, straight-chain or branched C$_1$–C$_4$ alkoxy, straight-chain or branched C$_1$–C$_4$ alkoxycarbonyl or optionally substituted straight-chain or branched C$_1$–C$_4$ alkyl wherein the substituents on the alkyl group are hydroxyl or straight-chain or branched alkoxy having up to 3 carbon atoms,
D represents hydrogen, cyclobutyl, cyclopentyl, cyclohexyl, cycloheptyl, cyclooctyl or straight-chain or branched alkyl having up to 10 carbon atoms,
E represents the —CO— or —CS— group,
L represents a group of the formula —NR$^9$,
wherein
R$^9$ denotes hydrogen or straight-chain or branched alkyl having up to 5 carbon atoms, which is optionally substituted by hydroxyl or phenyl,
R$^5$ represents phenyl which is optionally substituted up to 2 times by identical or different substituents selected from the group consisting of nitro, carboxyl, fluorine, chlorine, bromine, cyano, straight-chain or branched C$_1$–C$_4$ alkenyl, straight-chain or branched C$_1$–C$_4$ alkoxycarbonyl or optionally substituted straight-chain or branched C$_1$–C$_5$ alkyl wherein the substituents on the alkyl group are hydroxyl, carboxyl or straight-chain or branched alkoxy or alkoxycarbonyl each having up to 5 carbon atoms,
or said phenyl ring is optionally further substituted by a group of the formula —OR$^{10}$ or —NR$^{11}$R$^{12}$,
wherein
R$^{10}$ denotes hydrogen or straight-chain or branched alkyl or alkenyl each having up to 4 carbon atoms,
R$^{11}$ and R$^{12}$ are identical or different and denote phenyl, hydrogen or straight-chain or branched alkyl having up to 5 carbon atoms or denote straight-chain or branched acyl having up to 6 carbon atoms, which is optionally substituted by a group of the formula —NR$^{13}$R$^{14}$,
wherein
R$^{13}$ and R$^{14}$ are identical or different and denote hydrogen or straight-chain or branched acyl having up to 6 carbon atoms,
R$^6$ represents hydrogen, carboxyl or straight-chain or branched alkoxycarbonyl having up to 4 carbon atoms, or represents straight-chain or branched alkyl having up to 5 carbon atoms, which is optionally substituted by hydroxyl or by a group of the formula —O—CO—R$^{15}$,
wherein
R$^{15}$ denotes phenyl which is optionally substituted up to 3 times by identical or different fluorine, chlorine, bromine or hydroxyl substituents or by straight-chain or branched alkyl having up to 4 carbon atoms, or straight-chain or branched alkyl or alkenyl each having up to 20 carbon atoms, each of which is optionally substituted by a group of the formula —OR$^{16}$,
wherein
R$^{16}$ is hydrogen, benzyl, triphenylmethyl or straight-chain or branched acyl having up to 5 carbon atoms,
R$^7$ represents hydrogen, or
R$^6$ and R$^7$ together represent the group of the formula =O,
or an isomeric form of said compound or a salt thereof.

3. The method of claim 1, wherein
R$^1$ and R$^2$ form a pyridyl ring which is optionally substituted 1 to 2 times by identical or different substituents;
R$^3$ and R$^4$, including the double bond connecting them, form a phenyl ring or a 6-membered cycloalkene ring each of which are optionally substituted 1 to 2 times by identical or different substituents,
wherein said substituents on the pyridyl, phenyl or cycloalkene ring are selected from the group consisting of fluorine, chlorine, bromine, trifluoromethyl, carboxyl, hydroxyl, straight-chain or branched $C_1$–$C_3$ alkoxy, straight-chain or branched $C_1$–$C_3$ alkoxycarbonyl or optionally substituted straight-chain or branched $C_1$–$C_3$ alkyl, wherein the substituents on the alkyl group are hydroxyl, methoxy or ethoxy, D represents hydrogen, cyclopentyl, cyclohexyl, cycloheptyl, cyclooctyl or straight-chain or branched alkyl having up to 6 carbon atoms, E represents the —CO— or —CS— group, L represents a group of the formula —$NR^9$,
wherein
$R^9$ denotes hydrogen or straight-chain or branched alkyl having up to 4 carbon atoms, which is optionally substituted by hydroxyl or phenyl, $R^5$ represents phenyl, which is optionally substituted up to 2 times by identical or different substituents selected from the group consisting of nitro, carboxyl, fluorine, chlorine bromine, cyano, $C_1$–$C_3$ alkenyl, straight-chain or branched $C_1$–$C_3$ alkoxycarbonyl or optionally substituted straight-chain or branched $C_1$–$C_4$ alkyl wherein the substituents are hydroxyl, carboxyl or straight-chain or branched alkoxy or alkoxycarbonyl each having up to 4 carbon atoms,
or said phenyl ring is optionally further substituted by a group of the formula —$OR^{10}$ or —$NR^{11}R^{12}$,
wherein
$R^{10}$ denotes hydrogen or straight-chain or branched alkyl or alkenyl each having up to 3 carbon atoms,
$R^{11}$ and $R^{12}$ are identical or different and denote phenyl, hydrogen or straight-chain or branched alkyl having up to 4 carbon atoms or denote straight-chain or branched acyl having up to 5 carbon atoms, which is optionally substituted by a group of the formula —$NR^{13}R^{14}$,
wherein
$R^{13}$ and $R^{14}$ are identical or different and denote hydrogen or staight-chain or branched acyl having up to 5 carbon atoms, $R^6$ represents hydrogen, carboxyl or straight-chain or branched alkoxycarbonyl having up to 3 carbon atoms, or represents straight-chain or branched alkyl having up to 4 carbon atoms, which is optionally substituted by hydroxyl or by a group of the formula —O—CO—$R^{15}$,
wherein
$R^{15}$ denotes phenyl which is optionally substituted up to 3 times by identical or different straight-chain or branched alkyl having up to 3 carbon atoms, or denotes straight-chain or branched alkyl or alkenyl each having up to 19 carbon atoms, each of which is optionally substituted by a group of the formula —$OR^{16}$,
wherein
$R^{16}$ is hydrogen, benzyl, triphenylmethyl or straight-chain or branched acyl having up to 4 carbon atoms, $R^7$ represents hydrogen or
$R^6$ and $R^7$ together represent the group of the formula =O,
or an isomeric form of said compound or a salt thereof.

4. The method of claim 1, wherein
$R^1$ and $R^2$ form a pyridyl ring which is optionally substituted 1 to 3 times by identical or different substituents;
$R^3$ and $R^4$, including the double bond connecting them, form a phenyl ring or a 6-membered cycloalkene ring each of which are optionally substituted 1 to 3 times by identical or different substituents,
wherein said substituents on the pyridyl, phenyl or cycloalkene ring are selected from the group consisting of fluorine, chlorine, bromine, trifluoromethyl, carboxyl, hydroxyl, straight-chain or branched $C_1$–$C_4$ alkoxy, straight-chain or branched $C_1$–$C_4$ alkoxycarbonyl or optionally substituted straight-chain or $C_1$–$C_4$ alkyl wherein the substituents on the alkyl group are hydroxyl or straight-chain or branched alkoxy having up to 3 carbon atoms, D represents hydrogen, cycloalkyl having 4 to 12 carbon atoms or straight-chain or branched alkyl having up to 12 carbon atoms, E represents the —CO— or —CS— group, L represents a group of the formula —$NR^9$,
wherein
$R^9$ denotes hydrogen or straight-chain or branched alkyl having up to 6 carbon atoms, which is optionally substituted by hydroxyl or phenyl, $R^5$ represents phenyl which is optionally substituted 1 to 3 times by identical or different substituents selected from the group consisting of nitro, carboxyl, halogen, cyano, straight-chain or branched $C_2$–$C_6$ alkenyl, straight-chain or branched $C_1$–$C_6$ alkoxycarbonyl or optionally substituted $C_1$–$C_6$ straight-chain or branched alkyl wherein the substituents on the alkyl are hydroxyl, carboxyl or straight-chain or branched $C_1$–$C_6$ alkoxy or straight-chain or branched $C_1$–$C_6$ alkoxycarbonyl,
or said phenyl ring is further optionally substituted by a group of the formula —$OR^{10}$ or —$NR^{11}R^{12}$,
wherein
$R^{10}$ denotes hydrogen or straight-chain or branched alkyl or alkenyl each having up to 6 carbon atoms,
$R^{11}$ and $R^{12}$ are identical or different and denote phenyl, hydrogen or straight-chain or branched alkyl having up to 6 carbon atoms or straight-chain or branched acyl having up to 8 carbon atoms, which is optionally substituted by a group of the formula —$NR^{13}R^{14}$,
wherein
$R^{13}$ and $R^{14}$ are identical or different and denote hydrogen or straight-chain or branched acyl having up to 8 carbon atoms, $R^6$ represents hydrogen or straight-chain or branched alkyl having up to 6 carbon atoms which is optionally substituted by hydroxyl, $R^7$ represents hydrogen,
or an isomeric form of said compound or a salt thereof.

5. The method of claim 1, wherein
$R^1$ and $R^2$ form a pyridyl ring which is optionally substituted 1 to 3 times by identical or different substituents;
$R^3$ and $R^4$, including the double bond connecting them, form a phenyl ring or a 6-membered cycloalkene ring each of which are optionally substituted 1 to 3 times by identical or different substituents,
wherein said substituents on the pyridyl, phenyl or cycloalkene ring are selected from the group consisting of fluorine, chlorine, bromine, trifluoromethyl, carboxyl, hydroxyl, straight-chain or branched $C_1$–$C_4$ alkoxy, straight-chain or branched $C_1$–$C_4$ alkoxycarbonyl or optionally substituted straight-chain or branched $C_1$–$C_4$ alkyl wherein the substituents on the alkyl group are hydroxyl or straight-chain or branched alkoxy having up to 3 carbon atoms, D represents hydrogen, cycloalkyl having 4 to 12 carbon atoms or straight-chain or branched alkyl having up to 12 carbon atoms, E represents the —CO— or —CS— group, L represents a group of the formula —$NR^9$,
  wherein
    $R^9$ denotes hydrogen or straight-chain or branched alkyl having up to 6 carbon atoms, which is optionally substituted by hydroxyl or phenyl, $R^5$ represents phenyl which is optionally substituted 1 to 3 times by identical or different substituents selected from the group consisting of nitro, carboxyl, halogen, cyano, straight-chain or branched $C_2$–$C_6$ alkenyl, straight-chain or branched $C_1$–$C_6$ alkoxycarbonyl or optionally substituted $C_1$–$C_6$ straight chain or branched alkyl wherein the substituents on the alkyl are hydroxyl, carboxyl or straight-chain or branched $C_1$–$C_6$ alkoxy or straight-chain or branched $C_1$–$C_6$ alkoxycarbonyl, or said phenyl ring is further optionally substituted by a group of the formula —$OR^{10}$ or —$NR^{11}R^{12}$,
  wherein $R^6$ represents straight-chain or branched alkyl having up to 6 carbon atoms which is substituted by hydroxyl, or an isomeric form of said compound or a salt thereof.

* * * * *